US006997929B2

(12) United States Patent
Manzi et al.

(10) Patent No.: US 6,997,929 B2
(45) Date of Patent: Feb. 14, 2006

(54) TISSUE DISTRACTION DEVICE

(75) Inventors: Richard J. Manzi, Yorktown Heights, NY (US); Joseph N. Logan, Trumbell, CT (US); Steven J. Wysocki, Stratford, CT (US); Frank S. Bono, Collierville, TN (US); Spanky A. Raymond, Uniontown, OH (US)

(73) Assignee: Spine Wave, Inc., Shelton, CT (US)

( * ) Notice: Subject to any disclaimer, the term of this patent is extended or adjusted under 35 U.S.C. 154(b) by 0 days.

(21) Appl. No.: 10/846,235

(22) Filed: May 14, 2004

(65) Prior Publication Data

US 2004/0230198 A1 Nov. 18, 2004

Related U.S. Application Data

(60) Provisional application No. 60/471,015, filed on May 16, 2003.

(51) Int. Cl.
*A61B 17/58* (2006.01)

(52) U.S. Cl. ........................................................ 606/90
(58) Field of Classification Search .................. 606/61, 606/90, 99, 198; 623/17.11, 17.16
See application file for complete search history.

(56) References Cited

U.S. PATENT DOCUMENTS

| | | | | |
|---|---|---|---|---|
| 3,486,505 A | * | 12/1969 | Morrison | 606/90 |
| 5,192,327 A | * | 3/1993 | Brantigan | 623/17.11 |
| 5,571,109 A | * | 11/1996 | Bertagnoli | 606/61 |
| 6,159,211 A | * | 12/2000 | Boriani et al. | 606/61 |
| 6,478,800 B1 | * | 11/2002 | Fraser et al. | 606/99 |
| 6,562,074 B1 | | 5/2003 | Gerbec et al. | |
| 6,595,998 B1 | * | 7/2003 | Johnson et al. | 606/90 |
| 6,648,917 B1 | | 11/2003 | Gerbec et al. | |
| 6,656,178 B1 | * | 12/2003 | Veldhuizen et al. | 606/61 |
| 6,837,904 B1 | * | 1/2005 | Ralph et al. | 623/17.16 |
| 6,852,129 B1 | | 2/2005 | Gerbec et al. | |
| 6,863,673 B1 | | 3/2005 | Gerbec et al. | |
| 2003/0171812 A1 | * | 9/2003 | Grunberg et al. | 623/17.11 |
| 2004/0019354 A1 | * | 1/2004 | Johnson et al. | 606/90 |
| 2004/0064144 A1 | * | 4/2004 | Johnson et al. | 606/90 |
| 2004/0220580 A1 | * | 11/2004 | Johnson et al. | 606/90 |

* cited by examiner

*Primary Examiner*—Eduardo C. Robert
*Assistant Examiner*—David Comstock
(74) *Attorney, Agent, or Firm*—Maginot, Moore & Beck

(57) ABSTRACT

An apparatus and method for distracting, in a given direction, and supporting two tissue surfaces is provided. A plurality of wafers are consecutively inserted using a wafer insertion apparatus between the two tissue surfaces to create a column of wafers. A detachable wafer assembly is provided that includes a base wafer initially associated with a track assembly of a wafer insertion apparatus. The base wafer is dislodged from the track assembly so that the base wafer is left within the distraction site as the track assembly is removed. A top cap wafer is provided that is situated at the top of the wafer stack, in which the top cap wafer is larger than the remaining wafers to form a gap surrounding the stack to receive biologic material.

29 Claims, 20 Drawing Sheets

TISSUE DISTRACTION DEVICE

REFERENCE TO RELATED APPLICATION

This application claims priority to now abandoned provisional application No. 60/471,015, filed on May 16, 2003, in the name of the present inventors. The disclosure of this provisional application No. 60/471,015 is incorporated herein by reference.

FIELD OF THE INVENTION

The present invention involves the field of surgery, and particularly surgical instruments and methods of using the same.

BACKGROUND OF THE INVENTION

A variety of physical conditions involve two tissue surfaces that, for treatment of the condition, need to be distracted from one another and then supported away from one another. Such distraction may be to gain exposure to select tissue structures, to apply a therapeutic pressure to select tissues, to return tissue structures to their anatomic position and form, or in some cases to deliver a drug or growth factor to alter, influence or deter further growth of select tissues. Depending on the condition being treated, the tissue surfaces may be opposed or contiguous and may be bone, skin, soft tissue, or a combination thereof. An optimal treatment method includes distracting and supporting the tissue surfaces simultaneously.

A minimally invasive distraction and support device would have significant application in orthopaedic surgical procedures, including acute and elective procedures to treat bone fractures and degenerative changes of the skeletal system and including vertebral compression fractures, interbody fusion, vertebral disc augmentation or replacement, and other compression fractures including, but not limited to tibial plateau compression fractures, calcaneous compression fractures, distal tibia fractures, distal radius (wrist) fractures, crushed or fractured orbit and orthopaedic oncology. Further, a minimally invasive distraction and support device would have application in non-orthopaedic surgical procedures in plastic surgery (for example facial reconstruction), gastrointestinal surgery and urological surgery (for example the treatment of incontinence).

One technique used to treat vertebral compression fractures is injection of bone filler into the fractured vertebral body. This procedure is commonly referred to as percutaneous vertebroplasty. Vertebroplasty involves injecting bone filler (for example, bone cement) into the collapsed vertebra to stabilize and strengthen the crushed bone. In this procedure, lower viscosities and higher pressures tend to disperse the bone filler throughout the vertebral body. However, such conditions dramatically increase the risk of bone filler extravasation from the vertebral body.

Kyphoplasty is a modified vertebral fracture treatment that uses one or two balloons, similar to angioplasty balloons, to attempt to reduce the fracture and restore vertebral height prior to injecting the bone filler. Two balloons are typically introduced into the vertebra via bilateral transpedicular cannulae. The balloons are inflated to reduce the fracture. After the balloon(s) is deflated and removed, leaving a relatively empty cavity, bone cement is injected into the vertebra. In theory, inflation of the balloons restores vertebral height. However, it is difficult to consistently attain meaningful height restoration. It appears the inconsistent results are due, in part, to the manner in which the balloon expands in a compressible media and the structural orientation of the trabecular bone within the vertebra.

A tibial plateau fracture is a crushing injury to one or both of the tibial condyles resulting in a depression in the articular surface of the condyle. In conjunction with the compression fracture, there may be a splitting fracture of the tibial plateau. Appropriate treatment for compression fractures depends on the severity of the fracture. Minimally displaced compression fractures may be stabilized in a cast or brace without surgical intervention. More severely displaced compression with or without displacement fractures are treated via open reduction and internal fixation.

Typically, the underside of the compression fracture is accessed either through a window cut (a relatively small resection) into the side of the tibia or by opening or displacing a splitting fracture. A bone elevator is then used to reduce the fracture and align the articular surface of the tibial condyle. A fluoroscope or arthroscope may be used to visualize and confirm the reduction. Bone filler is placed into the cavity under the reduced compression fracture to maintain the reduction. If a window was cut into the side of the tibia, the window is packed with graft material and may be secured with a bone plate. If a splitting fracture was opened to gain access, then the fracture is reduced and may be stabilized with bone screws, bone plate and screws, or a buttress plate and screws. Both of these methods are very invasive and require extensive rehabilitation.

Spinal fusion is most frequently indicated to treat chronic back pain associated with instability or degenerative disc disease that has not responded to less invasive treatments. Fusion is also prescribed to treat trauma and congenital deformities. Spinal fusion involves removal of the spinal disc and fusing or joining the two adjacent vertebrae. The primary objective for patients suffering from instability is to diminish the patient's pain by reducing spinal motion.

Spinal fusions are generally categorized into two large groups: instrumented and non-instrumented. In non-instrumented procedures, the physician removes tissue from the unstable disc space and fills it with some form of bone graft that facilitates the fusion of the two adjacent vertebral bodies. Instrumented procedures are similar to non-instrumented procedures, except that implants (generally metallic) are also applied to further stabilize the vertebrae and improve the likelihood of fusion.

In all interbody surgical approaches, a relatively large opening is made in the annulus. The nuclear material is removed and the end plates are decorticated to facilitate bony fusion. Overall, the use of interbody devices has resulted in mixed clinical outcomes. Placement of a fixed height device presents challenges in proper tensioning of the annulus. For these and other reasons, there is concern over long-term stability of interbody devices and fusion mass.

A need remains for a system and method for distracting or elevating adjacent tissues that is minimally invasive and more easily implemented. Moreover, the system and method should provide a simplified capability for quantifying and controlling the amount of distraction. The system and method should also permit additional augmentation of the distraction site.

SUMMARY OF THE INVENTION

The invention provides a combination of a temporary or long term implantable device and instrumentation to place the device, in which tissue surfaces are distracted along an axis to enable access to the space between the tissues.

Generally, the invention provides wafers for stacking upon one another to provide an axially extending column to distract and support tissue surfaces. While a primary use of the invention is to reduce and stabilize vertebral compression fractures, the invention may be used in any situation where it is desirable to distract two tissue surfaces. The tissue may be bone, skin, soft tissue, or combinations thereof. Further, the surfaces may be opposed surfaces of contiguous elements or surfaces of opposed elements. Thus, the invention may be used to treat vertebral compression fractures, for replacement of vertebral discs, as an interbody fusion device, wedge opening high tibial osteotomy, tibial tuberosity elevation, as well as for treating other compression fractures including, but not limited to tibia plateau fractures, calcaneous, distal tibial fractures, or distal radius (wrist) fractures. The invention may also be used for restoring the floor of the orbit, for elevating soft tissue in cosmetic applications, or in incontinence applications as a urethral restrictor. Alternately, the invention may be used in similar veterinary applications.

The terms "vertical", "up", etc., are occasionally used herein for ease of understanding, and these terms should be taken in reference to the vertebrae of a standing patient. Thus, "vertical" refers generally to the axis of the spine. We may also utilize mutually perpendicular "X", "Y" and "Z" axes to describe configurations and movement, with the Z-axis being the axis of the column of wafers, that is, the direction in which this column grows as wafers are added sequentially to it. The X-axis refers to the axis extending generally in the direction of movement of each wafer as it is advanced to a position beneath a preceding wafer, and the Y-axis is perpendicular to both the X- and Z-axes. The wafers are sometimes described with reference to permitted degrees of freedom or restraint when they are placed in a column. It should be understood that these permitted degrees of freedom or restraint refer to the permitted or restrained movement of one wafer with respect to an adjacent wafer along one or more of the three axes, and the permitted or restrained rotation between adjacent wafers about one or more of these axes.

The distraction device includes a plurality of stackable wafers designed for insertion between tissue surfaces to form a column. The wafer column is assembled in vivo to provide a distraction force as well as support and stabilization of the distracted tissue. Preferably, the wafers place distraction force in one direction only and thus provide directional distraction. The distraction device may be permanently implanted, in which case the wafer column may be used alone or in conjunction with a bone filler material. Alternately, the distraction device may be used temporarily to manipulate tissues and then removed.

In use, the wafers are preferably stacked between two tissue surfaces as they are implanted, thereby distracting and supporting the tissue surfaces simultaneously. In the vertebral compression fracture application, it is preferable to distract along the Z-axis (along the axis of the spine) to restore vertebral height. However, in other applications, it may be preferable to provide distraction in a different direction. The features of a wafer and a column of wafers will be described relative to position and direction. The top of a wafer or the top of the column is defined as the face of the wafer or column in the direction of distraction. The bottom of a wafer or the bottom of the column is defined as the face opposite the top face. In similar fashion, above and below a wafer or column implies along the top and bottom of the wafer or column, respectively. Each wafer has a leading edge that enters the forming column first and a trailing edge opposite the leading edge. The sides of the wafer are adjacent the leading and trailing edges and the top and bottom faces of the wafer. In general, the sides are longer than the leading and trailing edges, however the sides may be shorter than the leading and trailing edges. The axis of the column is defined as a line parallel to the direction of distraction.

In order to place the wafers between the tissue surfaces, a wafer inserter is positioned within the surgical site with access at its distal tip to the tissue surfaces to be distracted and supported. In one embodiment, a wafer is placed on the track and a plunger is used to advance the wafer to the distal end of the track. This is repeated with consecutive wafers until a column of sufficient height is created per physician discretion. After the wafer(s) have been inserted, the insertion apparatus is removed. The distal end of the insertion apparatus may be manufactured from the same material as the wafers and/or be detachable. In this embodiment, the distal end of the insertion instrument would be detached after placing the wafer column, and the instrument removed.

In another embodiment, the wafer inserter can be configured for one-hand operation. The wafer inserter includes a handle/trigger assembly that is configured to receive a replaceable wafer cartridge. The cartridge carries a number of wafers to be sequentially inserted into the distraction space by the wafer inserter. Preferably, the cartridge is biased, meaning that constant pressure is applied to the last wafer of the stack to continually advance wafers to the discharge end of the cartridge. The handle/trigger assembly includes a finger trigger that operates a linkage mechanism to advance a wafer pusher.

In certain embodiments, the wafer inserter includes a dual track assembly mounted to the handle/trigger assembly. The dual track assembly includes a bottom track and a top track with a wafer "stay" that prevents retrograde motion of a wafer on the way to the distraction site. The top track serves as a carrier for traversing a series of wafers from the cartridge to a delivery end of the track assembly. The bottom track accepts an individual wafer from the top track near the tip or delivery end of the track assembly and place that wafer in proper position before being advanced or pushed into the distraction site. Wafer stays hold the position of wafers in transit within the track assembly as the pusher and advancing mechanisms are retracted for a subsequent firing.

The wafer inserter can further include a wafer finger advancer and pusher mechanism. The finger advancer conveys each wafer on by one with every squeeze of the trigger of the handle/trigger assembly. With every actuation of the trigger, the finger advancer advances each wafer within the track assembly incrementally farther down the track to the track tip. In certain embodiments, the finger advancer can include a series of raised fingers that engage the bottom rear of each wafer.

The pusher mechanism preferably resides within the lower track and is configured to push a wafer positioned within the lower track into the distraction site. The pusher mechanism is also actuated by movement of the trigger of the handle/trigger assembly.

In another embodiment, a detachable wafer assembly is provided in which the end of the insertion apparatus constitutes a wafer component that is detached and left in situ. In one embodiment, the detachable wafer assembly includes a base wafer and a top cap wafer that, in effect, sandwich intermediate wafers inserted between the base and top cap wafers. The base and top cap wafers are pre-loaded onto a bottom track of a wafer insertion apparatus prior to insertion of the apparatus into the tissue space to be distracted. The base wafer operates as a stop for successive wafers advanced along the wafer insertion apparatus so that the advanced wafers are positioned at the discharge end of the bottom track. As the first additional wafer is advanced, it dislodges the top cap wafer from the bottom track and pushes it upward into the working space. Each subsequently advanced wafer pushes the stack upward until the top cap contacts the upper limit of the space to be distracted.

Once the stack of wafers is complete, the base wafer is disassociated from the bottom track of the wafer insertion apparatus. Once the base wafer is so disassociated, the bottom track can be removed, leaving the entire stack, including the base wafer, in the distracted space with little or no change in overall distracted height.

In one embodiment, the base wafer includes a number of bosses projecting from the bottom surface of the wafer. The bosses pass through openings in an intermediate slide cutter and engage within receptacles or bores defined in the bottom track of the wafer insertion apparatus. In one embodiment, the bosses can be initially press-fit within the receptacles so that the base wafer is held firmly in position while other wafers are inserted into the working space. In the preferred embodiment, the bosses are integral with the remainder of the base wafer and are formed of the same material as the wafer. The slide cutter, and particularly the boss openings, includes cutting edges that are used to sever the bosses from the base wafer as the slide cutter is retracted within the bottom track. Once the bosses are severed, the base wafer is disassociated from the wafer insertion apparatus and can remain in situ when the apparatus is removed from the tissue.

In another embodiment, the base wafer is initially held in position by interaction of retention posts on the bottom track with retention notches on the base wafer. In addition, a release plate is interposed between the base wafer and the bottom track. The release plate includes a ramp or cam surface that pushes the base wafer upward to dislodge the retention notches form the retention posts, thereby allowing the bottom track to be removed without disturbing the base wafer within the tissue space.

In a further embodiment, the bottom track includes a split line at its working end that allows lateral portions of the track to separate. The split line defines a retention slot that received a retention key on the underside of the base wafer. Thus, the base wafer is initially held in position by interaction of the retention key with the retention slot in the bottom track. A release plate is interposed between the base wafer and bottom track. The release plate defines a release cam on its bottom surface that initially rests within a notch in the split line of the bottom track. As the release plate is withdrawn, the cam exits the retention notch and travels along the split line, causing the lateral portions of the track to separate. As these portions separate along the split line, the retention slot widens allowing the retention key on the bottom of the base wafer to exit the retention slot and remain in situ as the bottom track and wafer insertion apparatus is retracted and removed.

In one embodiment of the invention, a method is provided for sequentially inserting wafers, stackable consecutively one upon another to form a column extending in the given direction, into a space to be distracted. The method comprises the steps of providing a wafer channel having a top cap wafer removably supported on a distal end thereof adapted to be inserted into the space to be distracted, and providing a source of wafers to be inserted into the space. The wafers are sequentially conveyed from the source through the wafer channel into the space to be distracted to form a stack of wafers within the space. The top cap wafer is dislodged as the wafers are sequentially conveyed into the space to be distracted.

In certain embodiments, the top cap wafer has a planar area greater than the planar are of the remaining wafers in the stack. The larger top cap wafer forms a gap around the remaining wafers as the top cap wafer is advanced within the distracted space. The method then can include the additional step of injecting a biologic material into that gap.

In another aspect of the invention, an apparatus is provided for sequentially inserting wafers, stackable consecutively one upon another to form a stack extending in a given direction into a space to be distracted. The apparatus comprises a source of wafers, a track assembly configured to sequentially advance wafers from the source of wafers into the space to be distracted, the track having a distal end and a defining a channel at the distal end, and a base wafer supported on the channel of the track assembly, the base wafer defining a support surface for supporting subsequent wafers advanced thereon by the track assembly. In one feature of this embodiment, a connection mechanism is disposed between the channel and the base wafer that is configured to releasably connect the base wafer to the channel.

In a specific embodiment, the connection mechanism includes at least one bore defined in the channel, and a corresponding boss projecting from the base wafer and sized for engagement within the bore. The apparatus further comprises a slide cutter slidably disposed within the channel, the slide cutter defining at least one opening therethrough corresponding to the at least one bore and configured to receive the corresponding boss therethrough when the boss is engaged within the bore. In one feature, the opening is configured to sever the boss from the base wafer when the cutter is translated within the channel. In certain embodiment, the channel defines a wafer channel sized for passage of the wafers therethrough, and the track assembly is configured to support the base wafer beneath the wafer channel. The channel further defines a cutter channel beneath the base wafer when the base wafer is supported on the channel for slidably receiving the slide cutter therein.

In an alternative embodiment, connection mechanism includes at least one retention post projecting from the channel, and a corresponding retention notch defined in the base wafer to engage the retention post when the base wafer is within the channel. This embodiment further comprises a release plate slidably disposed within the channel, the release plate having a surface configured to contact the base wafer and dislodge the corresponding retention notch from the at least one retention post when the release plate is translated within the channel.

In yet another alternative embodiment, the connection mechanism includes: a retention slot defined in the channel, and a key projecting from the base wafer and configured to be received within the retention slot when the base wafer is disposed within the channel. With this embodiment, a split line is defined in the channel and intersecting the retention slot, and a release plate is slidably disposed within the channel. The release plate has an element extending through the split line and configured to separate the channel along the split line as the release plate is translated within the channel, whereby the retention slot expands as the channel is separated to release the key from the retention slot.

In one feature of the invention, the channel of the apparatus defines a wafer channel sized for passage of the wafers therethrough. The track assembly is configured to support the base wafer beneath the wafer channel.

Another embodiment of the invention contemplates an apparatus for sequentially inserting wafers, stackable consecutively one upon another to form a column extending in the given direction, into a space to be distracted, the apparatus that comprises a source of wafers, a track assembly adapted to sequentially advance wafers from the source of wafers into the space to be distracted, and a top cap wafer removably engaged with a distal end of the track assembly disposed within the space to be distracted, the top cap wafer adapted to be dislodged by the sequentially advanced wafers. With this embodiment, the track assembly includes a track defining a wafer channel sized to receive a wafer advanced therethrough, and the track assembly defines a surface for supporting the top cap wafer above the wafer channel at the distal end thereof.

In certain specific embodiments, the surface includes a pair of slots on opposite sides of the wafer channel, and the top cap wafer is configured to engage the pair of slots. In other specific embodiments, the wafers from the source of wafers define a first planar area and the top cap wafer defines a second planar area greater than the first planar area. In other embodiments, the wafers from the source of wafers define a first width, and the top cap wafer defines a second width greater than the first width.

The present invention further contemplates a system for distracting a space within a body comprising a series of bio-compatible wafers forming a stack within the space, a first one of the wafers in contact with a surface of the body defining the space, the first one of the wafers having a larger area than the remaining wafers in the stack. This system can further comprise a base wafer in contact with an opposite surface of the body defining the space, the base wafer having a planar dimension greater than the remaining wafers.

It is one general object of the invention to provide a system for distracting a space within a patient, such as a vertebral body. A more specific object is to distract the space using a stack of wafers formed of a bio-compatible material.

A further object is to provide a system for distracting a space that ensures proper alignment of the wafer stack, and that can avoid changes in the distraction height once the associated wafer insertion apparatus has been removed. These and other objects and benefits will become apparent upon consideration of the following written description and accompanying figures.

DESCRIPTION OF THE PREFERRED EMBODIMENTS

Figure 1:
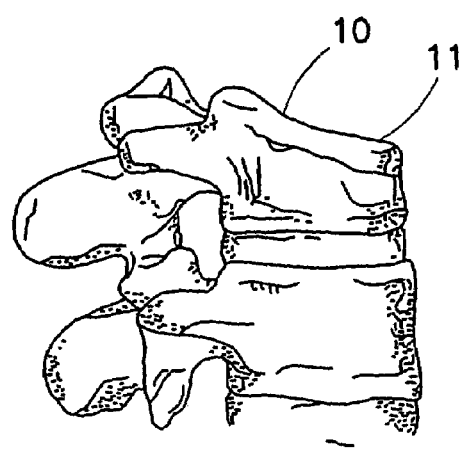
FIG. 1 shows a vertebral body having a compression fracture displacing its superior and anterior edge.

For the purposes of promoting an understanding of the principles of the invention, reference will now be made to the embodiments illustrated in the drawings and described in the following written specification. It is understood that no limitation to the scope of the invention is thereby intended. It is further understood that the present invention includes any alterations and modifications to the illustrated embodiments and includes further applications of the principles of the invention as would normally occur to one skilled in the art to which this invention pertains.

Figure 2:
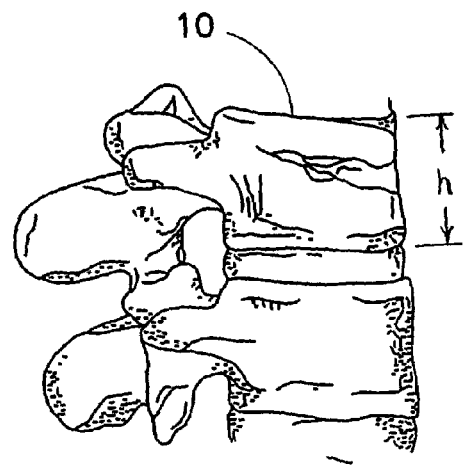
FIG. 2 shows a vertebral body, following treatment of a compression fracture.

The invention provides a combination of an implantable distraction device and instrumentation to place the device. The distraction device is detailed in this section by its application to the vertebral compression fracture. FIG. 1 shows a vertebral body 10 having a compression fracture displacing its superior and anterior edge 11. FIG. 2 shows a vertebral body 10 wherein the height has been restored.

In accordance with the present invention, a plurality of stackable wafers can be provided for insertion between two tissues and can be delivered to a surgical site along an axis transverse to the axis of distraction. Multiple wafer insertions result in a column of wafers at the surgical site that simultaneously distracts and supports the two tissues.

The wafers may be formed from a solid form of bone filler material, and/or any other suitable material such as, but not limited to, implantable grade alloys, medical grade composites, medical grade polymers, ceramics, hydrogels and resorbable polymers. The wafers may be dense or porous, while porous wafers may be filled with resorbable polymers, drug therapies or osteoinductive agents.

Figure 3:
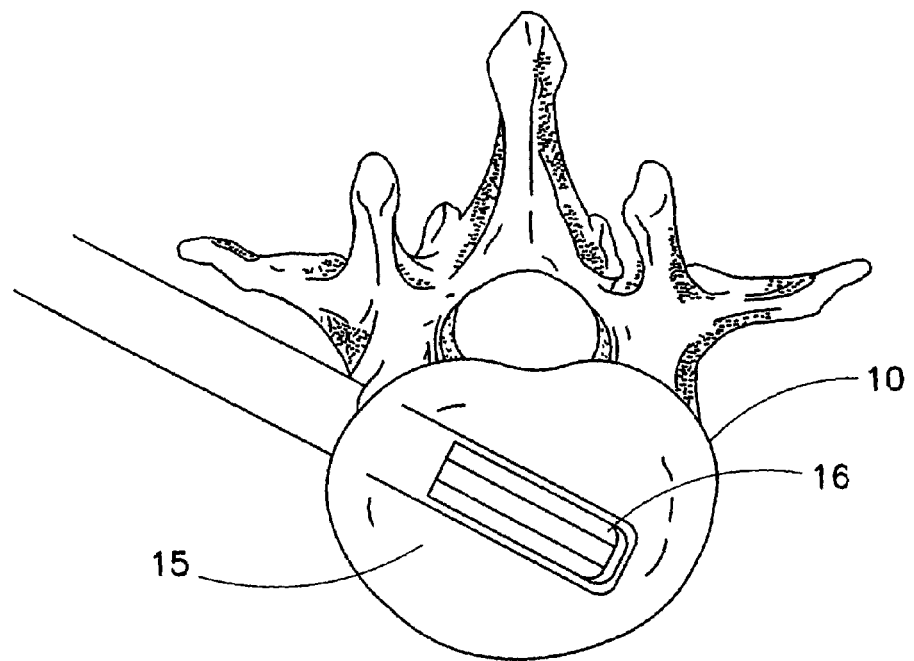
FIG. 3 illustrates a plan view of a distraction device insertion apparatus for use with an embodiment of the invention, placed within a vertebral body shown in cross-section.

The present invention provides that the wafer column is formed in vivo by using a wafer insertion apparatus. FIG. 3 illustrates the distal or discharge end portion 16 of a wafer insertion apparatus 15 placed within a vertebral body 10 with a wafer 18 positioned distally on the wafer insertion apparatus 15. During implantation, a plurality of such wafers 18 is stacked to form a column to restore vertebral height, such as the column 20 depicted in FIG. 5. Details of an exemplary wafer insertion apparatus 15 can be found in U.S. Pat. No. 6,595,998 [the '998 Patent], entitled "Tissue Distraction Device", which issued on Jul. 22, 2003, to the assignee of the present invention. The disclosure of this '998 Patent is incorporated herein by reference.

Consecutive wafer insertions result in a column of wafers at the surgical site. In one embodiment, the trailing edge of a wafer can be beveled or otherwise configured to guide the next wafer under the first. For instance, the wafer 22, depicted in FIG. 5, includes a beveled leading edge 23. This beveled edge 23 facilitates guiding the wafer under the trailing edge 24 of a preceding wafer 22. The trailing edge is correspondingly beveled to guide the subsequent wafer underneath.

The wafers 22 can have a variety of configurations and dimensions depending upon the particular surgical application. For instance, for vertebral compression fracture applications, exemplary wafer dimensions range as follows:

Wafer length between 5 mm and 50 mm;

Wafer width between 2 mm and 16 mm;

Wafer thickness between 0.2 mm and 6 mm; and

Curved wafer radii between 10 mm and 500 mm.

These dimensions are provided only as guidelines and any suitable dimensions may be used. Furthermore, the dimensions of the wafer will likely vary widely when the wafers are used in other applications, such as, for example, treating tibial plateau fractures.

In certain applications, it may be beneficial for the wafers to be secured to one another after insertion. Any suitable method for securing the wafers to one another as known by those skilled in the arts may be used. Wafers may be secured to one another by means of an adhesive bond, a chemical bond, and/or a mechanical interlock (as described above). Applying a generic fluent adhesive, for example cyanoacrylate, into the cavity surrounding the column provides adhesive bonding. The fluent adhesive hardens and locks the wafers.

The wafers may also include tunnels, grooves, or holes to facilitate movement of bone filler or other fluent materials through the wafer column into the surrounding bone. Further, openings may be provided through the wafers to allow communication between the tunnels, grooves, or holes or adjacent wafers. In any configuration, bone filler material injected into the wafer column would then flow through the column, fully encapsulating the wafers and better bonding the wafers to the bone filler. Further details of suitable wafers are disclosed in the '998 Patent, which details are again incorporated herein by reference.

Figure 5:
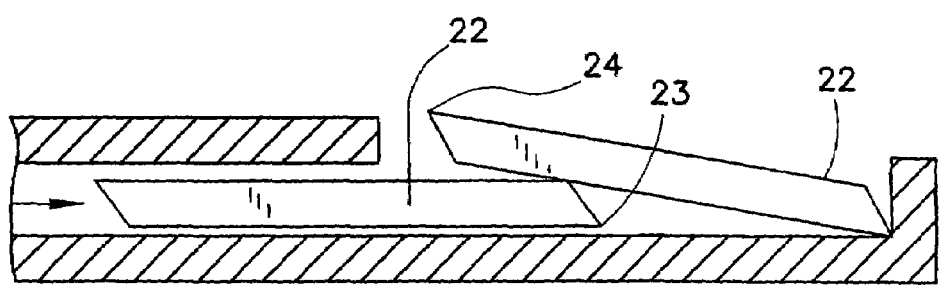
FIG. 5 illustrates a cross-sectional view of the insertion apparatus of FIG. 3 deploying a distraction device in a manner usable with an embodiment of the present invention.

In a clinical application, the wafers are inserted such that consecutive wafer insertions form a column 20, as shown in FIG. 5. The wafers in the column can be equally sized wafers, such as the intermediate wafers 26. Alternatively or in addition, the column can include larger top and bottom wafers 27, 28, respectively, to provide a larger surface area over which to distribute loads. Moreover, the larger wafers create a space or channel 30 between the edges of the intermediate wafers 26 and the surrounding tissue. This channel provides a path around the interspaced wafers through which a bone filler or other fluent material may flow to fully encapsulate the wafers and to interdigitate with surrounding tissue.

A wafer insertion apparatus is provided as part of the invention to deliver the wafers to the surgical site and to form a column of wafers. In one embodiment, the wafer insertion apparatus applies a force along the X-axis (the axis of insertion) to a wafer that is to be added to the column. As previously described, the wafers may be configured with beveled ends to facilitate growth of the column along the Z-axis (the vertical axis through the wafers) as the additional wafer is inserted.

Numerous variations of the wafer insertion apparatus are possible, the embodiments generally including, but not limited to, a track, a plunger, and a cartridge. The wafer insertion apparatus is comprised of a track, which is a long narrow channel through which wafers pass when placed into the wafer column. A plunger generally advances wafers down the track. Multiple wafers can be housed in a cartridge of the wafer insertion apparatus for advancement down the track. Preferably included is a mechanism for feeding subsequent wafers into the track in front of the plunger. Further, the track is configured for removal from the surgical site while leaving the wafer column intact.

Figure 6:
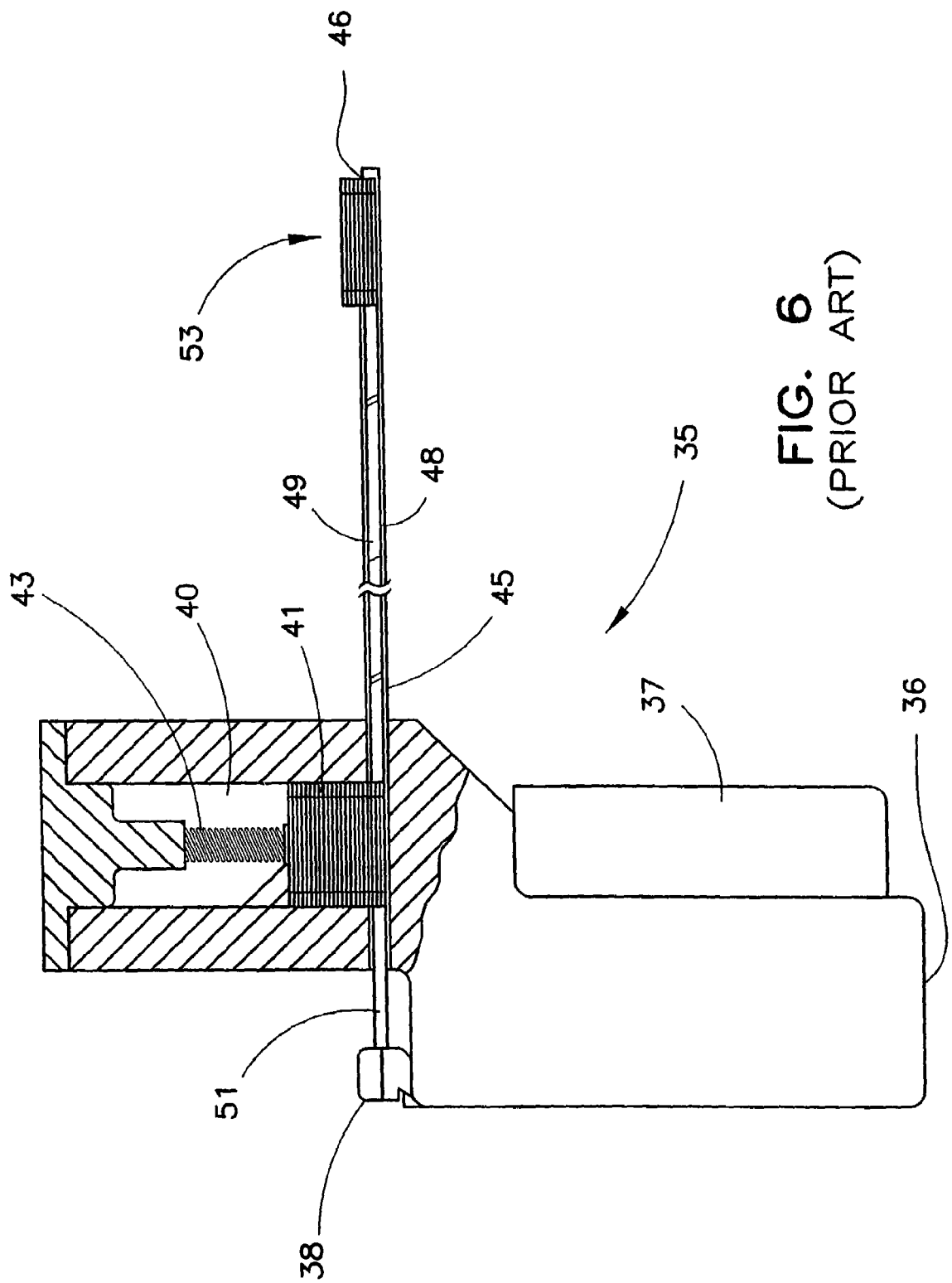
FIG. 6 shows a sectional view of an insertion apparatus usable with an embodiment of the present invention.

One embodiment of a wafer insertion apparatus 35 described in the '998 Patent is illustrated in FIG. 6. The handle 36 may be gripped to position the wafer insertion apparatus 35. The wafer insertion apparatus has, at its proximal end 38, a magazine 40 containing wafers 41. The wafers 41 may be stacked in the magazine 40 with a top surface of one wafer supporting the bottom surface of an adjacent wafer. The handle 36 is equipped with a trigger 37 for forcing wafers out of the magazine 40. Optionally, the magazine 40 is equipped with a spring 43 to load wafers 41 along a track 45 of the inserter 35. The track 45 extends from the magazine 40 to the surgical site at its distal end 46. As they enter the wafer track 45, the wafers 41 are aligned with the leading edge of one wafer adjacent the trailing edge of a preceding wafer. The track 45 in the wafer insert 35 shown in FIG. 6 includes a lower cavity 48 and an upper cavity 49. A plunger 51 extends through the lower cavity 48 while the wafers 41 are aligned along the upper surface of the plunger. An opening is provided along the top surface of the lower cavity 48 at the distal end 46 of the track 45 to accommodate a wafer. Thus, as the plunger is retracted past the trailing edge of the furthest distal wafer, the wafer drops into the lower cavity. The plunger pushes the wafer distally to form a column of wafers 53.

In an alternative embodiment of the invention, a wafer insertion apparatus 60 includes a wafer cartridge 61, a track assembly 63 and an advancement gun 65, as shown in FIGS. 7–16. Details of this wafer insertion apparatus can be found in co-pending U.S. patent application Ser. No. 10/813,819 [the '819 application], entitled "Tissue Distraction Device", which was filed on Mar. 31, 2004, and which is assigned to the owner of the present application. The disclosure of this co-pending '819 application is incorporated herein by reference; however, for purposes of illustration certain details of this apparatus 60 will be described below.

Figure 8:
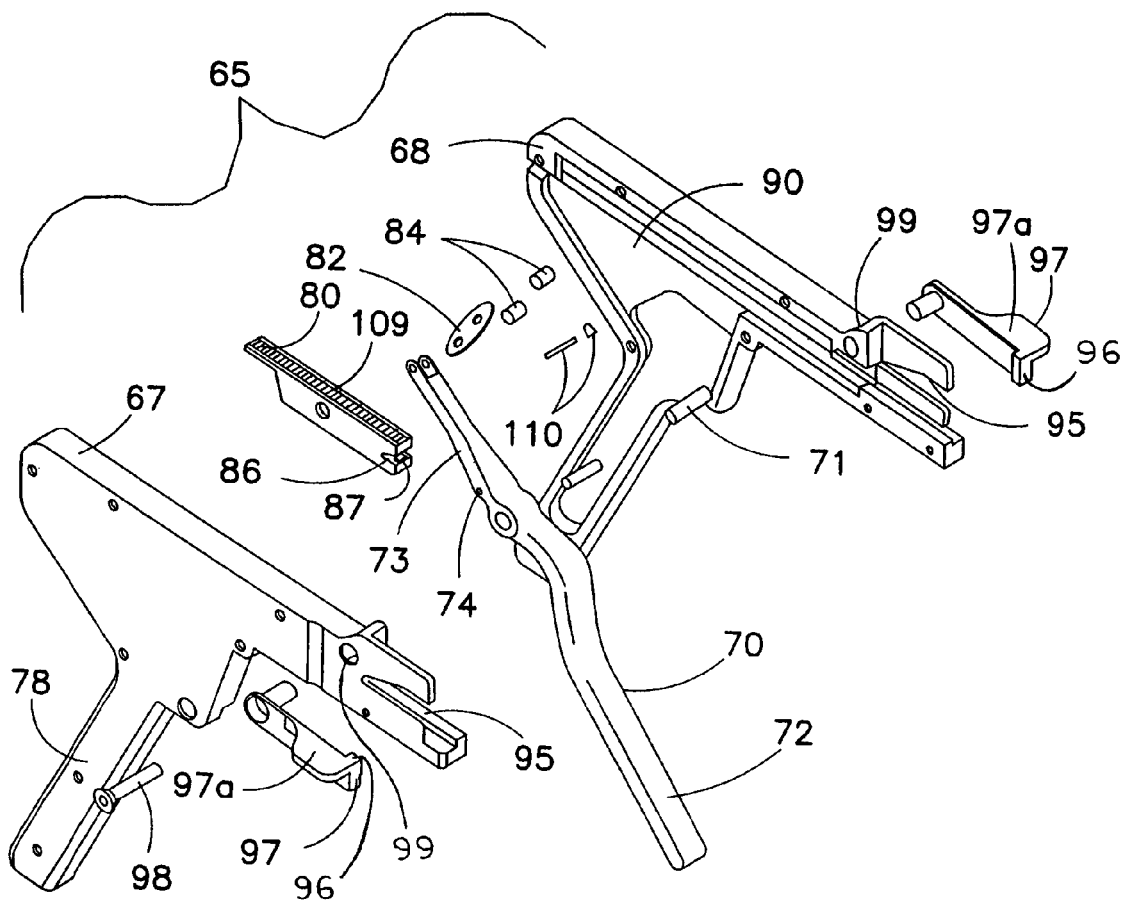
FIG. 8 is an exploded view of the advancement gun component of the wafer insertion apparatus shown in FIG. 7.
Figure 9:
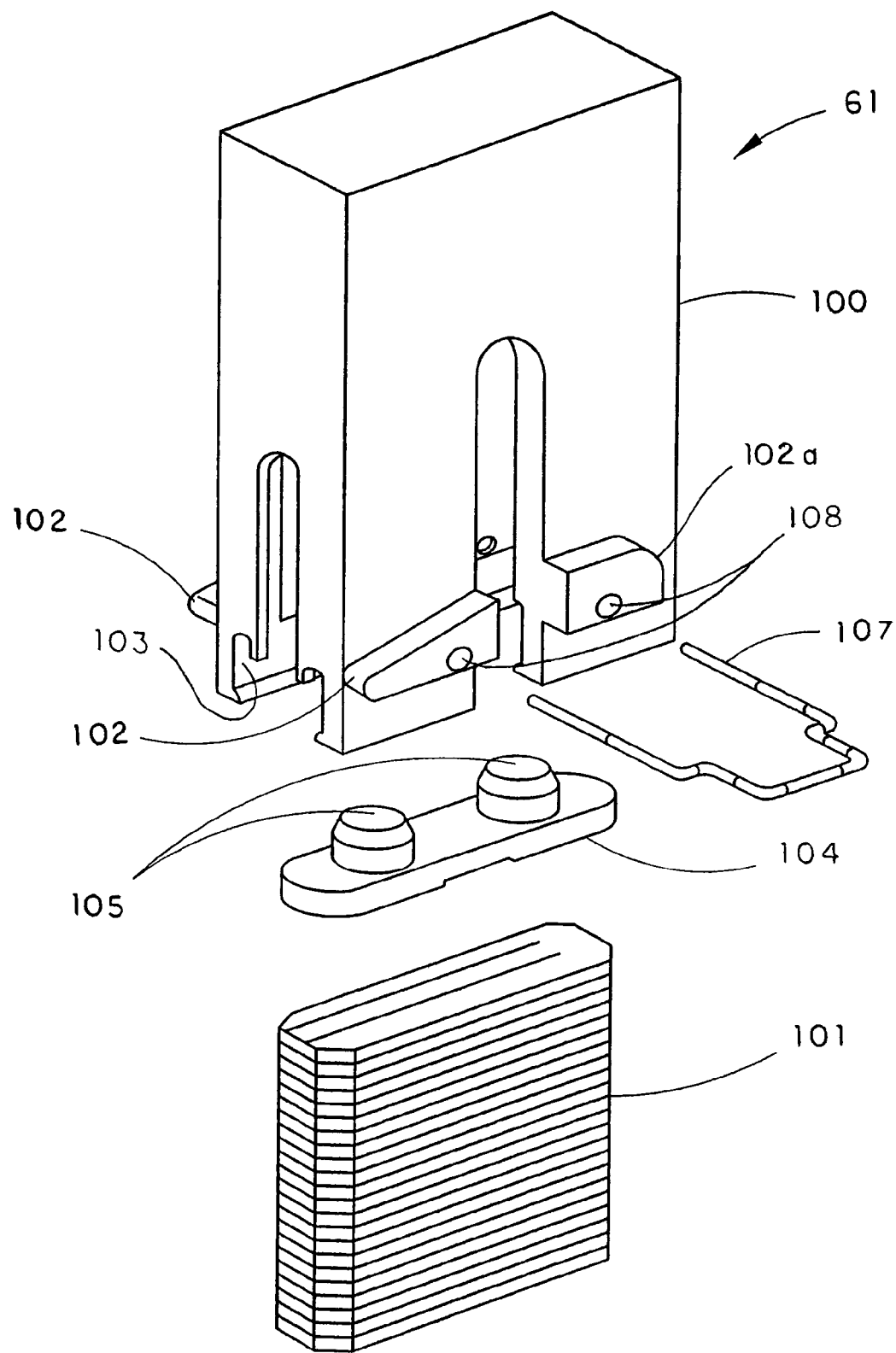
FIG. 9 is an exploded view of the wafer cartridge component of the wafer insertion apparatus shown in FIG. 7
Figure 10:
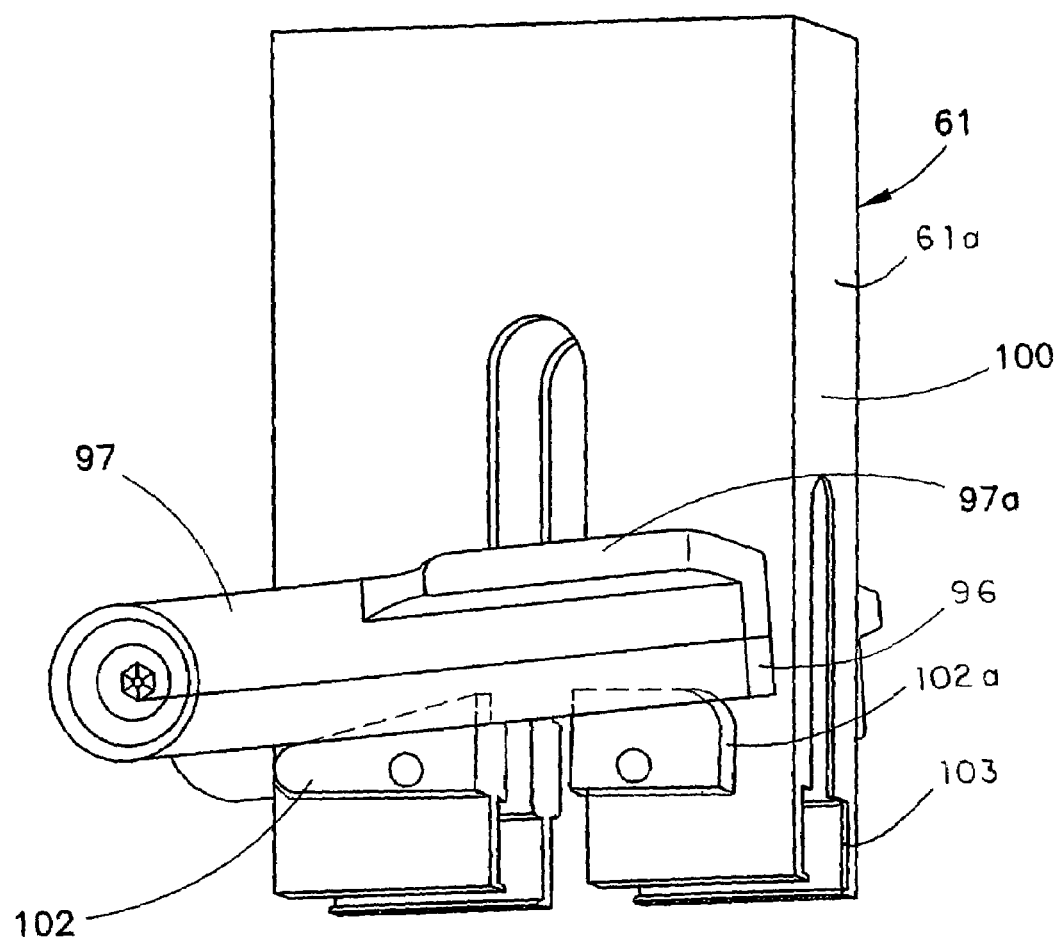
FIG. 10 is an enlarged view of the interface between the wafer cartridge component shown in FIG. 9 and a cartridge latch component of the wafer insertion apparatus shown in FIGS. 7 and 8.

Referring to the exploded view in FIG. 8, the advancement gun 65 includes left and right housings 67, 68 that can be coupled together in a known manner. Preferably, the housings are formed of a high-density plastic material that can be molded to define various interior and exterior features. The housings support a manual trigger 70 that is pivotably mounted to the housings 67, 68 by a pivot pin 71. The trigger 70 includes a manual grip 72 that is accessible outside the housings, and a lever arm 73 that operates within the housing. The lever arm 73 includes a return spring tab 74, seen best in FIG. 11, which provides a connection point for a return spring 76. The return spring 76 can be mounted within the handle 78 to apply a restorative force to the trigger 70 after it has been manually depressed and released.

Figure 11:
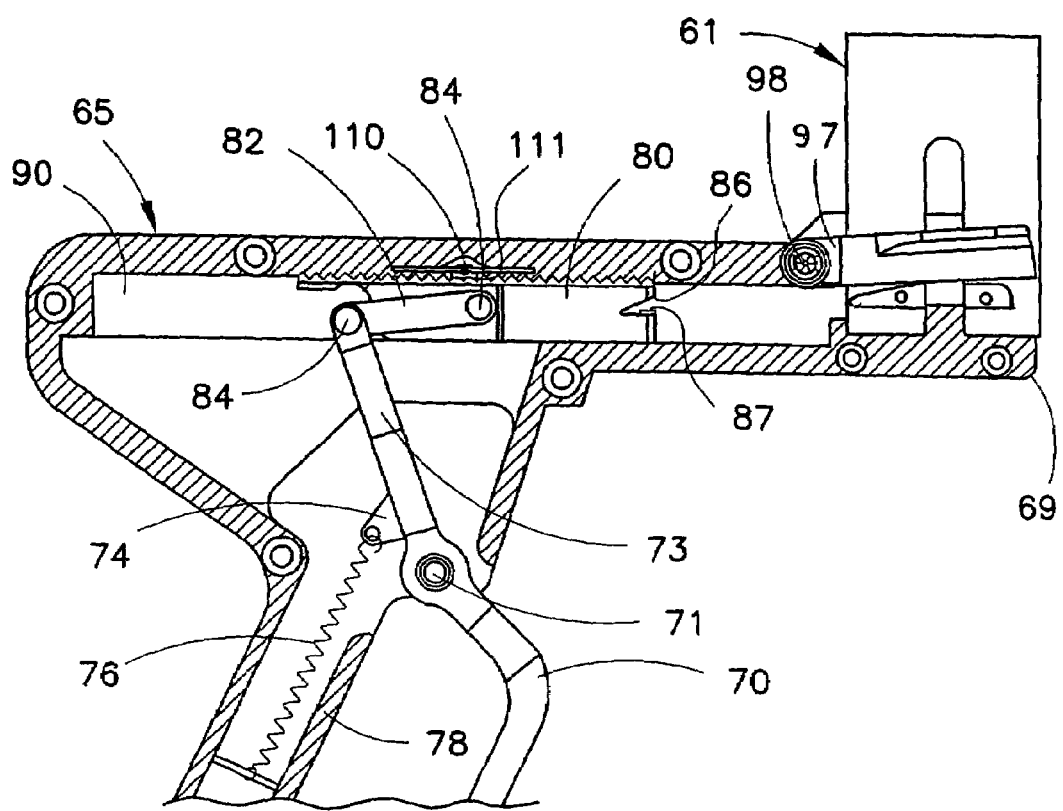
FIG. 11 is an enlarged side cut-away view of the wafer insertion apparatus shown in FIG. 7.
Figure 12:
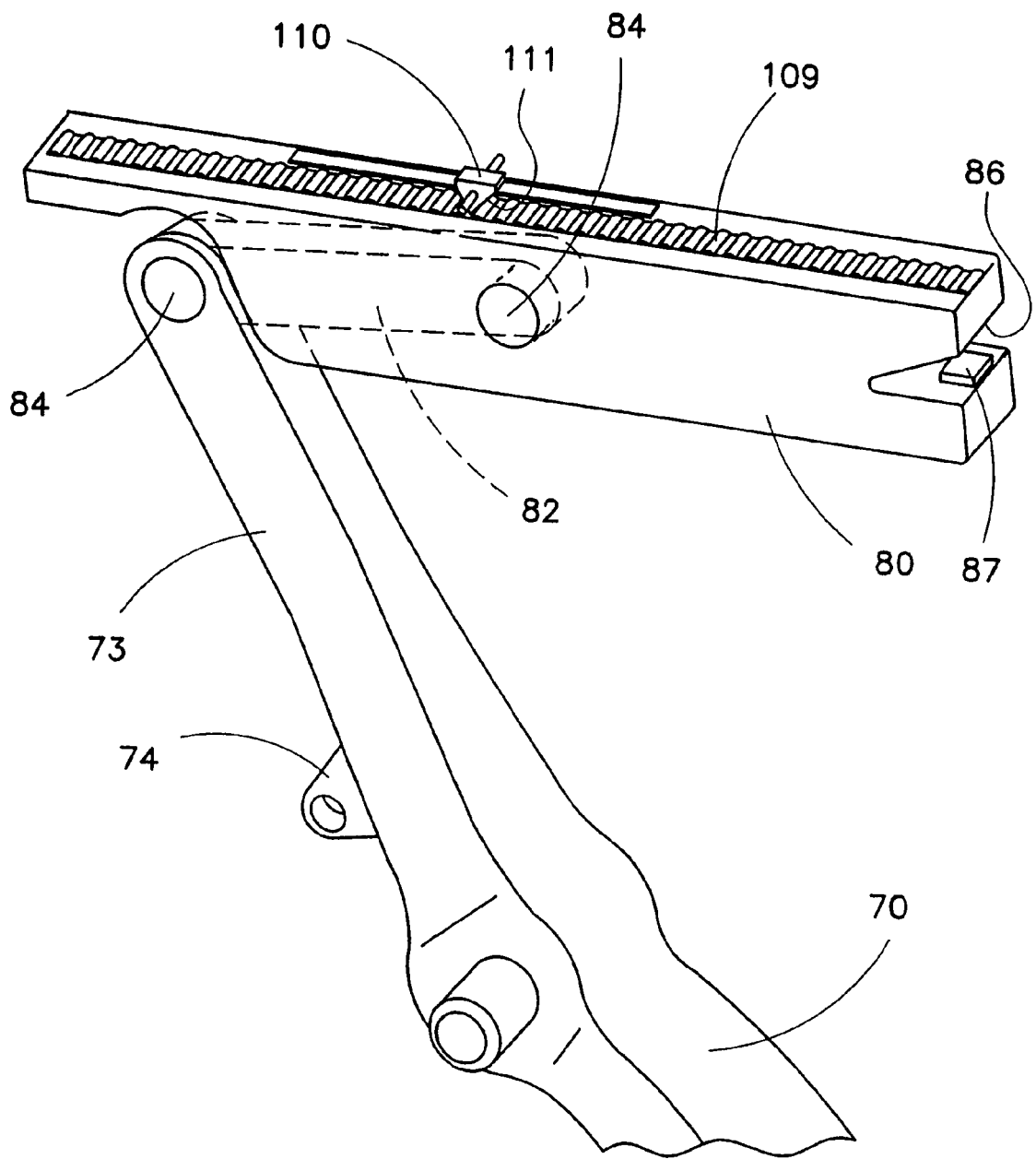
FIG. 12 is an enlarged perspective view of the trigger and advancer carriage components of the advancement gun shown in FIG. 8.

The advancement gun 65 includes a wafer advancement carriage 80 that is slidably disposed within an advancer channel 90 in the housings 67, 68, as shown in FIG. 11. The carriage 80 is connected to the lever arm 73 of the trigger 70 by way of a link 82. The link 82 is pivotably connected to the lever arm 73 and the carriage 80 by corresponding pivot pins 84, as depicted in FIGS. 11 and 12. As can be discerned from FIG. 11, when the trigger 70 is depressed, the lever arm 73 pivots in a clockwise direction, which pushes the link 82 against the carriage 80. Since the carriage is constrained within the channel 90, the pivoting movement of the trigger is translated to a linear movement of the carriage 80 toward the distal end 69 of the advancement gun 65. Each depression of the trigger constitutes one cycle of operation of the advancement gun, which corresponds to moving each wafer an incremental distance toward the discharge end 64 of the track assembly 63. This incremental distance is determined by the "throw" of the advancement gun, which in turn is related to the angle through which the trigger 70 can pivot within the gun. In the preferred embodiment, the throw of the advancement gun corresponds to a distance slightly greater than the length of a wafer.

The advancement gun 65 includes means for engaging a removable wafer cartridge, such as the cartridge 61. This feature allows a cartridge to be replaced while the apparatus is still in its operative position relative to the tissue surfaces being distracted. The distal end 69 of the advancement gun 65 defines engagement slots 95 that interface with locking cams 102 on opposite sides of the cartridge housing 100 (see FIG. 9). The cams 102 are configured to slide into the engagement slots 95. The advancement gun 65 includes latch halves 97 pivotably mounted to corresponding housing halves 67, 68 by a pivot pin 98 passing through a bore 99. The ends 96 of the latch halves 97 are turned inward to engage an end face 102a (FIG. 7) of the locking cams 102 on cartridge 61. When the latch ends engage the end face of the cartridge, they push the locking cams 102 into the slots 95. The latch halves can be provided with finger tabs 97a that can be pushed or pulled to engage or release the cartridge engagement means.

Referring again to FIG. 9, the cartridge 80 is shown with a housing 100 defining a cavity for receiving a stack of wafers 101. The cartridge can be provided pre-loaded so that the cartridge can be simply engaged to the advancement gun 65, and then removed and replaced once all the wafers have been discharged. The cartridge 61 can include a removable retainer clip 107 that spans the cavity in the housing 100 to hold the wafer stack 101 within the cartridge until it is needed. The arms of the clip 107 pass through openings 108 in the cartridge and underneath the stack 101. The retainer clip is kept in place as the cartridge is loaded in the advancement gun and then removed so that the stack 101 moves vertically into the gun.

In one embodiment, the cartridge 61 includes a spring plate 104 that is mounted on top of the stack 101. A spring arrangement (not shown) can be disposed between the spring plate 104 and the top of the housing 100 to provide pressure on the stack 101. The spring plate 104 can include a number of posts 105 configured to support the spring arrangement. The spring arrangement thus ensures that the lowermost wafer of the stack 101 is situated at the base of the cartridge during operation of the apparatus 60.

Turning back to FIGS. 8 and 11, the wafer advancement carriage 80 includes an advancer attachment notch 86 at its distal operating end. An attachment post 87 encroaches into the notch 86, as best seen in FIG. 12. The notch 86 and post 87 are provided for attaching an advancer or pusher 135 shown in FIG. 14. The pusher 135 includes an opening 139 at its proximal or engagement end 138. The engagement end 138 is configured to slide into the notch 86 of the carriage until the post 87 engages the opening 139 to lock the pusher 135 to the carriage 80.

As also shown in FIGS. 8 and 12, the carriage 80 includes an upper ratchet face 109. This ratchet face 109 engages a full throw assembly 110 that is configured to ensure that the carriage 80 travels through its full stroke before being allowed to return to its starting position (such as by operation of the return spring 76 connected to the trigger 70). The full throw assembly 110 includes a ratchet clip 111 that engages the ratchet face 109 of the carriage as the carriage is advanced toward the distal end 69 of the advancement gun. Thus, as long as the ratchet face 109 is in contact with the clip 111, the carriage cannot move on its return stroke. Once the carriage has been advanced far enough toward the distal end 69 so that the ratchet face 109 is clear of the clip, the carriage can be drawn back to its initial position by the lever arm 73 and link 82, preferably by operation of the spring 76. This feature ensures that the trigger will be fully depressed and a wafer advanced through a full cycle of movement. Absent this feature, a partial depression of the trigger could cause the wafer insertion apparatus to jam as a partially advanced or partially loaded wafer gets lodged within the track assembly 63.

Figure 13:
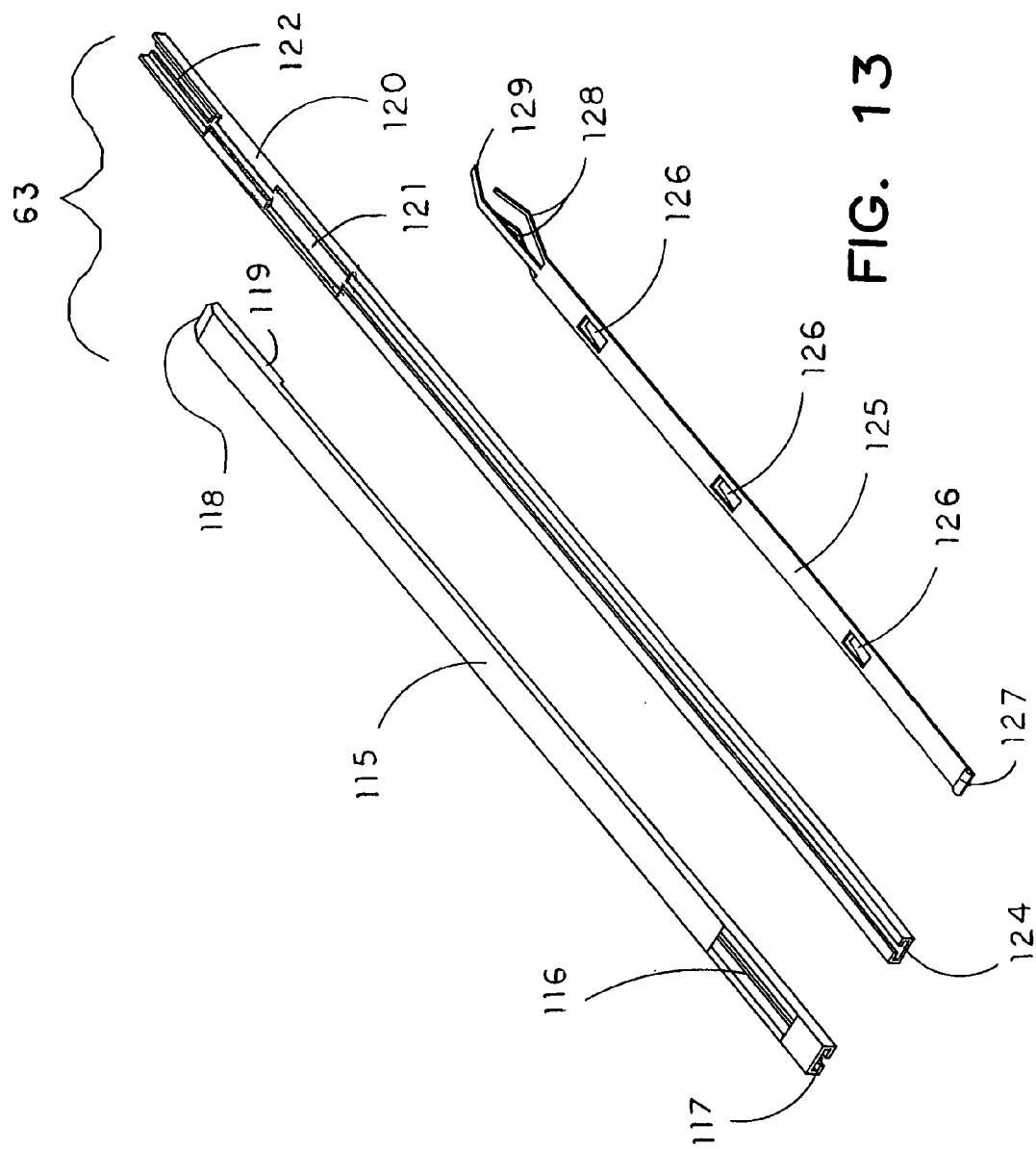
FIG. 13 is an exploded view of the track assembly component of the wafer insertion apparatus shown in FIG. 7.

Details of the track assembly 63 can be seen in FIG. 13. In the preferred embodiment, the track assembly 63 includes a top track 115, a bottom track 120 and a wafer stay 125. The track assembly 63 is mounted to the wafer cartridge 100, which is mounted to the distal end 69 of the advancement gun 65. In one embodiment, the end walls 61a of the wafer cartridge housing 100 define a slot 103 into which the track assembly 63 is mounted. The top track includes a wafer insertion opening 116 that is disposed immediately beneath the wafer stack 101 when the track assembly is mounted within the slot 103. The top track further defines a wafer channel 117 along its length that provides the initial path along which a succession of wafers can be advanced to the discharge end 64 (FIG. 7) of the apparatus. The end 118 of the top track is configured to engage the bottom track at a location 121. Preferably, the end 118 is configured to wrap around the bottom track at this location and can be suitably affixed so that the track assembly 63 is substantially rigid.

The channel 117 of the top track 115 retains the wafer stay 125, which functions to hold wafers within the channel 117 as the advancer/pusher mechanism 92 follows its return stroke (as explained below). A tab 127 at the proximal end of the wafer stay engages the distal end of the wafer insertion opening 116 to hold the stay in place. The wafer stay 125 includes a series of substantially evenly spaced intermediate prongs 126. The prongs 126 project downward at an angle into the wafer channel 117, facing the discharge end 64, as illustrated in FIG. 15(a). With this orientation, the prongs 125 do not impede forward movement of wafers along the channel. However, the prongs prevent retrograde movement since the free end of the prongs contact the back end of a wafer as it moves backward in the channel. Preferably, prongs 126 of the wafer stay 125 are formed of a material that is sufficiently firm to resist this retrograde movement, yet sufficiently flexible to deflect upward as a wafer passes underneath. For example, the prongs, as well as the entire wafer stay, may be formed of a thin gage stainless steel.

Again referring to FIG. 13, the bottom track 120 defines a pusher channel 124 that receives the advancer/pusher mechanism 92 (FIGS. 7 and 14) for reciprocating linear motion. The top track 115 is configured to overlie the bottom track 120 and engages the bottom track at the engagement end 118, as described above. It should be noted that the engagement end 118 is configured to provide an exit opening for a wafer that has traveled the length of the top track. The wafer thus exits the top track and drops into the bottom track 120 at the introduction slot 121.

In one aspect of the invention, the wafer stay 125 is configured to assist in this track change. In particular, in a preferred embodiment, the distal end of the wafer stay includes a pair of opposite spaced apart leaf springs 128. These leaf springs help maintain the wafer stay 125 within the top track 115 and also help keep the wafers in a proper orientation for entry into the introduction opening 121 of the bottom track, as best illustrated in FIG. 15(c). The wafer stay 125 also includes a dislodgement leaf spring 129 that is angled downward toward the bottom track. As a wafer moves toward the discharge/engagement end 118, the dislodgement leaf spring 129 pushes the wafer down into the introduction opening 121 of the bottom track 120. Once the wafer is within the bottom track, the pusher (FIG. 14) can be used to advance the wafer to the wafer discharge opening 122 of the bottom track 120. As explained above, this discharge opening is situated within the body space to be distracted.

Figure 14:
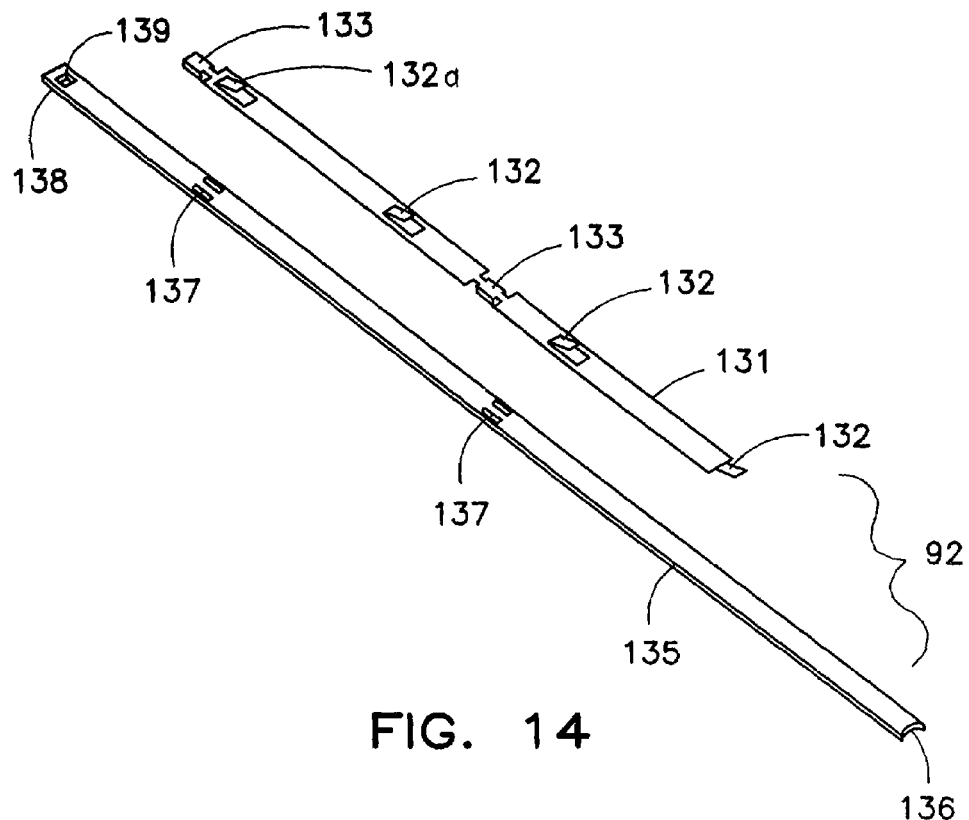
FIG. 14 is an exploded view of an advancer/pusher assembly for use with the wafer insertion apparatus shown in FIG. 7.
Figure 15:
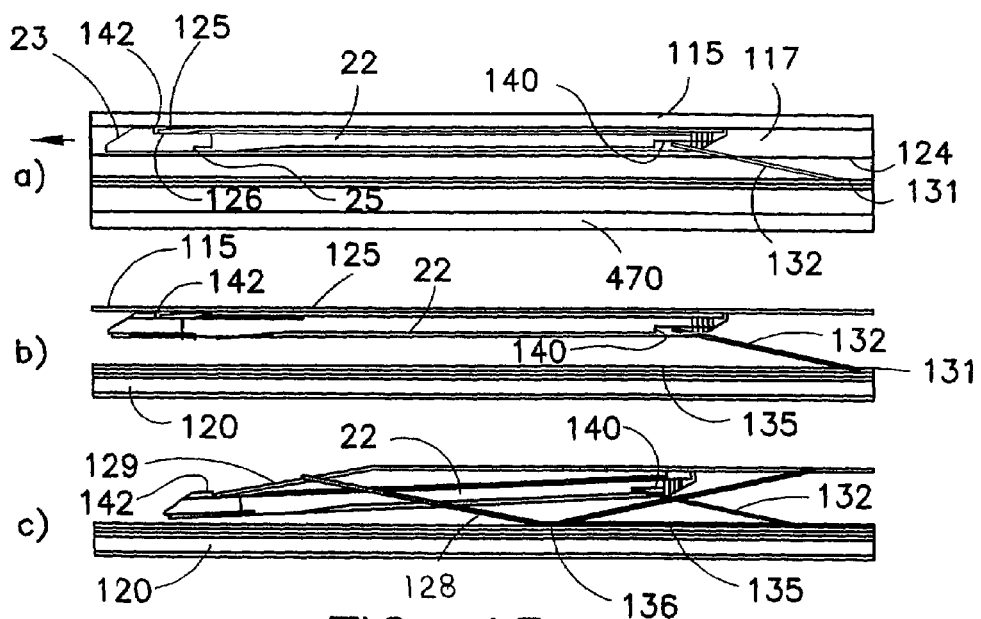
FIGS. 15(a)–15(c) are side partial views of the advancer/pusher shown in FIG. 14 mounted within the track assembly shown in FIG. 13 in different stages of operation to advance a wafer along the track assembly.
Figure 16:
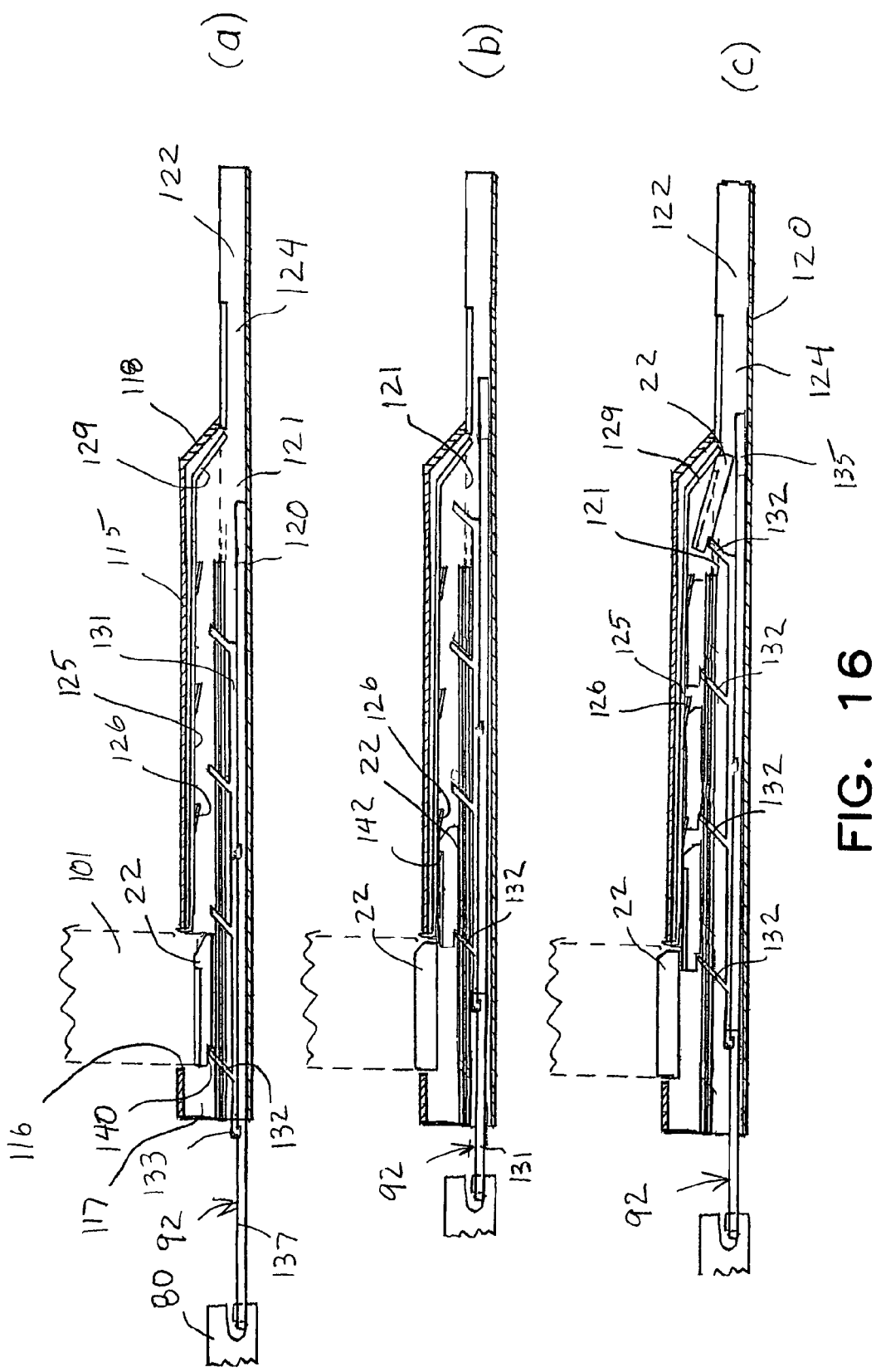
FIGS. 16(a)–(c) are side views of the apparatus depicting various stages of advancement of a wafer to the discharge end.

Details of the advancer/pusher mechanism 92 can be seen in FIG. 14. The mechanism includes an advancer 131 that includes a series of substantially evenly spaced fingers 132. These fingers project upward into the top track 115 when the advancer/pusher mechanism is disposed within the channel 124 in the bottom track 120, as shown in FIG. 15(b). Like the wafer stay 125, the fingers 132 on the inserter 131 are angled forward. This forward sweep of the fingers allows the inserter 131 to be retracted without pulling a wafer backward with it. As with the wafer stay, the fingers 132 are preferably spaced apart a distance slightly greater than the length of a wafer. In this way, the length of the tracks can be minimized and the regularity of the wafer insertion can be maintained.

The advancer 131 includes attachment clips 133 that engage attachment slots 137 in the pusher 135. Thus, the advancer 131 and pusher 135 are coupled and move together within the channel 124 of the bottom track. However, unlike the advancer, the pusher 135 essentially only operates on a wafer that is within the discharge opening 122 of the bottom channel. Thus, the pusher 135 includes a pusher end 136 that is configured to engage the proximal end of a wafer. The opposite end of the pusher defines an engagement end 138 and opening 139 that engage the wafer advancement carriage 80 as described above.

The operation of the track assembly 63 and advancer/pusher mechanism 92 can be understood from consideration of FIGS. 15(a)–(c). In FIG. 15(a), a wafer 22 is shown within the wafer channel 117 of the top track 115. The wafer includes a leading beveled end 23 that facilitates introduction of the wafer 22 underneath a previously advanced wafer disposed at the distraction site. The proximal end of the wafer preferably defines an advancement notch 140 that can be engaged by the wafer advancer 131 and the pusher 135. As shown in FIGS. 15(a)–(b), a finger 132 of the advancer 131 engages the notch 23 of the wafer 22 to push it along the top track 115 toward the distraction site. A prong 126 of the wafer stay 125 is also shown in FIG. 15(a), wherein the prong is deflected upward to allow passage of the wafer.

In one embodiment of the invention, the wafer 22 can be provided with a notch 142 at its leading end. Prongs 126 of the wafer stay 125 can resiliently drop into the notch 142 as the leading end of the wafer advances to prevent retrograde movement of the wafer. In the illustrated embodiment of FIG. 13, the wafer stay includes four prongs 126 to engage the notch 142 of three wafers situated within the wafer channel 117. In the illustrated embodiment, the prongs 126 are spaced along the top track by a distance slightly greater than the length of a wafer. Alternatively, a greater number of prongs can be provided, with the understanding that when the wafers sit within the wafer channel at the end of a stroke some prongs will engage the retrograde notches 142 of the wafers while other prongs will be resiliently compressed by the wafers.

As the wafer moves toward the engagement end 118 of the top track, the dislodgement leaf spring 129 of the wafer stay 125 contacts the wafer, as shown in FIG. 15(c). The spring 129 pushes the wafer downward into the bottom track 120. It can be seen in FIG. 15(c) that the pusher 135 is beneath the wafer. Once the wafer is disposed within the introduction opening 121 of the bottom track 570, the end 136 of the pusher can then contact the advancement notch 23 of the wafer. The advancer/pusher mechanism 92 is propelled toward the discharge end 64 of the apparatus, so the pusher end 136 continues to push the wafer until it is firmly positioned at the bottom of the distraction stack.

As should be apparent, the advancer/pusher mechanism 92 (including the connected advancer 131 and pusher 135) moves in the pusher channel 124 of the bottom track 120 relative to the stationary wafer stay 125, which is fixed within the wafer channel 117 of the top track 115. Thus, as the advancer/pusher mechanism 92 is retracted, the fingers 132 of the wafer advancer 131 slide along the bottom of the wafers remaining in the wafer channel 117 until the wafer advancement carriage 80 reaches the end of its return stroke. At this point, the rearmost prong 132a is situated beneath the wafer cartridge 61. A wafer from the stack 101 that has fallen into the opening 116 in the top track 115 is engaged by the finger 132a. When the trigger 70 is depressed again, the carriage 80 propels the advancer/pusher mechanism 92 to simultaneously propel one wafer into the wafer discharge opening 122 of the bottom track 120 and other wafers within the top track along the wafer channel 117. This procedure is repeated until the stack of wafers has been fully formed within the distracted body.

A sequence of events in the use of the insertion apparatus 60 is depicted in FIGS. 16(a)–(c). When the apparatus 60 is initially actuated, a wafer 22 is situated at the bottom of the wafer stack 101 within the wafer channel 117, as shown in FIG. 16(a). The advancement notch 140 of the wafer is engaged by a finger 132 of the wafer advancer 131. The remainder of the wafer channel 117 is empty. As the wafer advancement carriage 80 is translated forward (by depressing the trigger 70 of the advancement gun 65), the carriage pushes the wafer advancer 131, and ultimately the finger 132 advances the wafer along the top track 115, as shown in FIG. 16(b).

The wafer advancer 131 is shown near the end of its stroke in FIG. 16(b). When the advancer has been fully advanced, the wafer 22 is caught by the first prong 126 of the wafer stay 125. The advancer is then retracted with the carriage 80 until the advancer 131 is aligned under the wafer stack 101, as depicted in FIG. 16(a). The next wafer has already dropped through the opening 116 in the top track 115 and is awaiting engagement by the finger 132. The above steps are repeated and with each successive depression of the trigger the wafers 22 advance to the next prong 126 of the wafer stay.

On the fourth actuation of the advancement gun 65, the initial wafer 22 is in the position shown in FIG. 16(c). As explained above, the dislodgement prong 129 directs the wafer from the wafer channel 117 in the top track 115 to the pusher channel 124 in the bottom track 120. As the pusher 135 is retracted, the wafer is held in place within the wafer introduction slot 121. When the advancer/pusher mechanism 92 is fully retracted, the pusher 135 engages the advancement notch 140 in the lead wafer. Subsequent activation of the gun 65 causes the pusher 135 to propel the wafer into the discharge opening 122.

In the embodiment illustrated in FIGS. 7–16, the wafers are introduced into the body cavity from the bottom of the wafer stack. In other words, with this embodiment, each successive wafer pushes the previously stacked wafers upward to distract the space. Alternative embodiments of a wafer insertion apparatus are also disclosed in the '819 application, the description of which is also incorporated herein by reference. For instance, in one alternative embodiment, the wafers are stacked in the opposite direction. Thus, a wafer insertion apparatus 150 shown in FIGS. 17–18 includes an advancement gun 152 and a wafer cartridge supported on the underside of the gun. The track assembly 156 is supported by the gun. The gun includes a trigger 158 that reciprocates a wafer advancement carriage 160 engaged to an advancement/pusher mechanism 162. All of these components can be configured similar to the prior embodiments, except that they are modified to advance each wafer onto the top of the stack within the body cavity.

Figure 17:
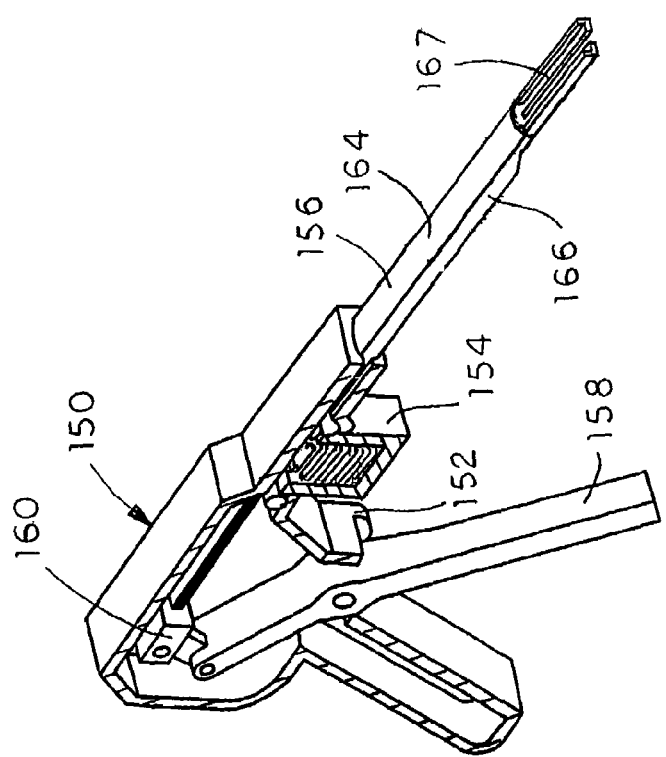
FIG. 17 is perspective cut-away view of a wafer insertion apparatus according to a further embodiment of the invention.

The track assembly 156 includes a top track 164 and a bottom track 166 that are essentially the analog of the bottom track 120 and top track 115, respectively, of the previous embodiment. Thus, each wafer exits the apparatus 150 from a discharge opening 167 in the bottom track 166. The moving components of the apparatus 150 can be configured similar to the like components of the previous embodiment, except that components of the apparatus 150 of FIGS. 17–18 are switched between the top and bottom tracks from those in the apparatus 60.

Figure 18:
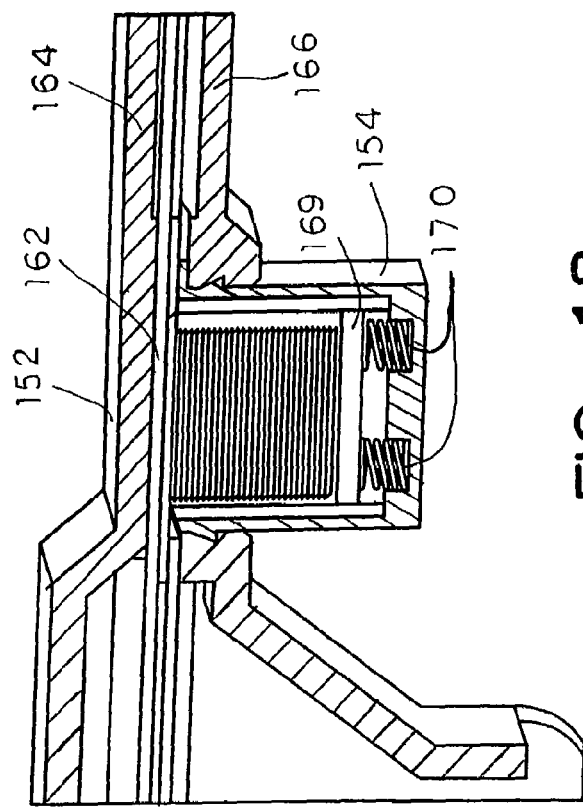
FIG. 18 is a side cross-sectional view of the wafer cartridge portion of the apparatus shown in FIG. 17.

As shown in FIG. 18, the wafer cartridge 154 is mounted to the underside of the advancement gun 152. Thus, each wafer is fed upward into the bottom track 166 and into engagement with the advancement/pusher mechanism 162. In order to drive the stack into the advancement mechanism, a spring plate 169 is biased upward into the wafer stack by an arrangement of springs 170. This arrangement is similar to the spring biased stack described above in connection with the apparatus 60.

Figure 19:
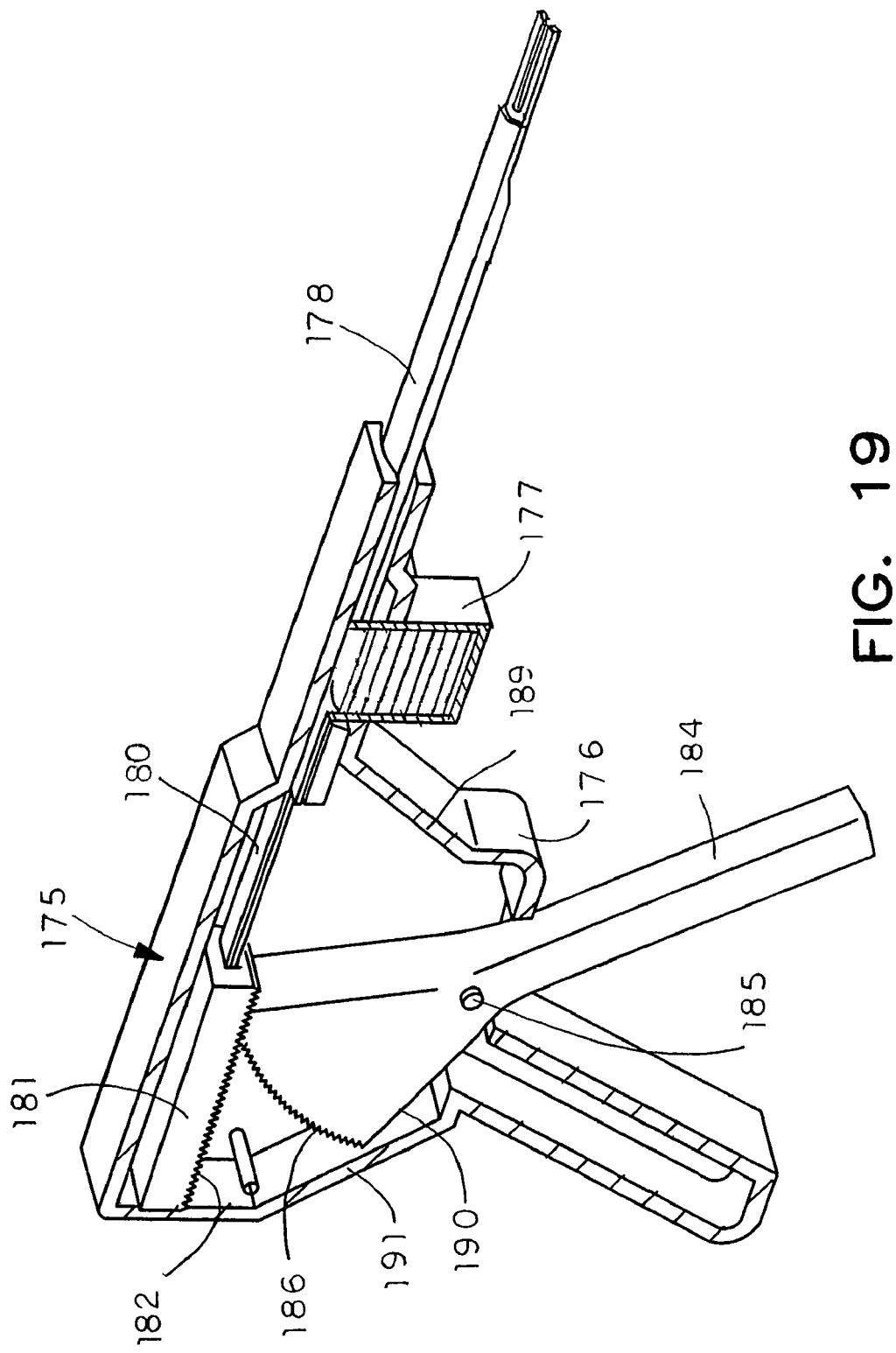
FIG. 19 is a perspective cut-away view of a wafer insertion apparatus according to a further embodiment of the invention.

The present invention contemplates a trigger driven advancement/pusher mechanism, such as the mechanism 92 described above. In the previous embodiments, the trigger, such as trigger 70, is connected to a carriage 80 by a floating link 82. Other trigger or actuation mechanisms are contemplated by the invention. For example, in one alternative embodiment, a wafer insertion apparatus 175 includes an advancement gun 176, a bottom loaded cartridge 177 and a track assembly 178, as shown in FIG. 19. An advancement/pusher mechanism 180 is engaged to a carriage 181 that is slidably disposed in the gun, in a fashion similar to the embodiments described above.

The gun further includes a trigger 184 that is pivotably engaged to the gun at a pivot mount 185. In this embodiment, the carriage 181 includes a rack gear 182 facing the trigger. The trigger 184 includes a clock gear 186 that meshes with the rack gear 182 as the trigger is pivoted. Thus, the drive interface between the trigger and the carriage is direct, without any intermediate linkage structure.

In a further aspect of this embodiment, the trigger 184 defines a stop face 188. This stop face contacts a stop wall 189 of the advancement gun 176 to prevent further pivoting of the trigger. More significantly, when the trigger can no longer pivot, the translation of the carriage 181 stops, signifying the end of the stroke of the advancement/pusher mechanism 180. With this feature, the full throw assembly 110 (FIG. 8) can be eliminated. Similarly, the back face 190 of the trigger 184 can contact a rear stop wall 191 to limit the return movement of the trigger, and therefore the carriage.

Figure 4:
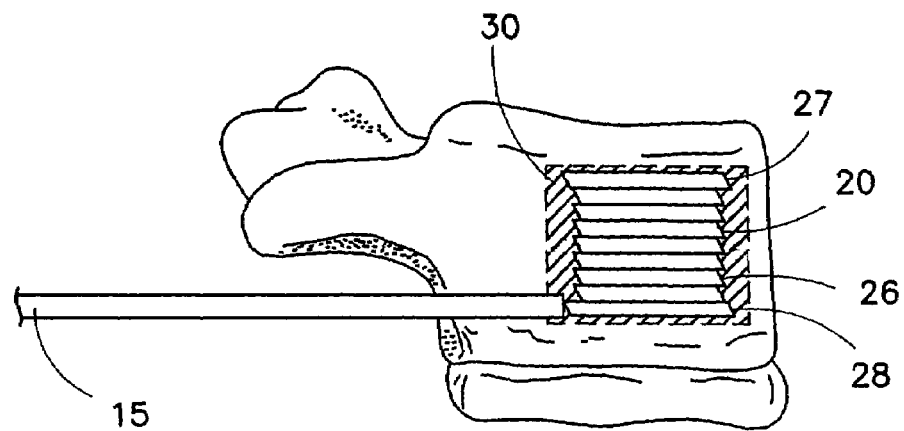
FIG. 4 shows a plan view of a further configuration of distraction device being deployed within a vertebral body, shown in sectional view.
Figure 20:
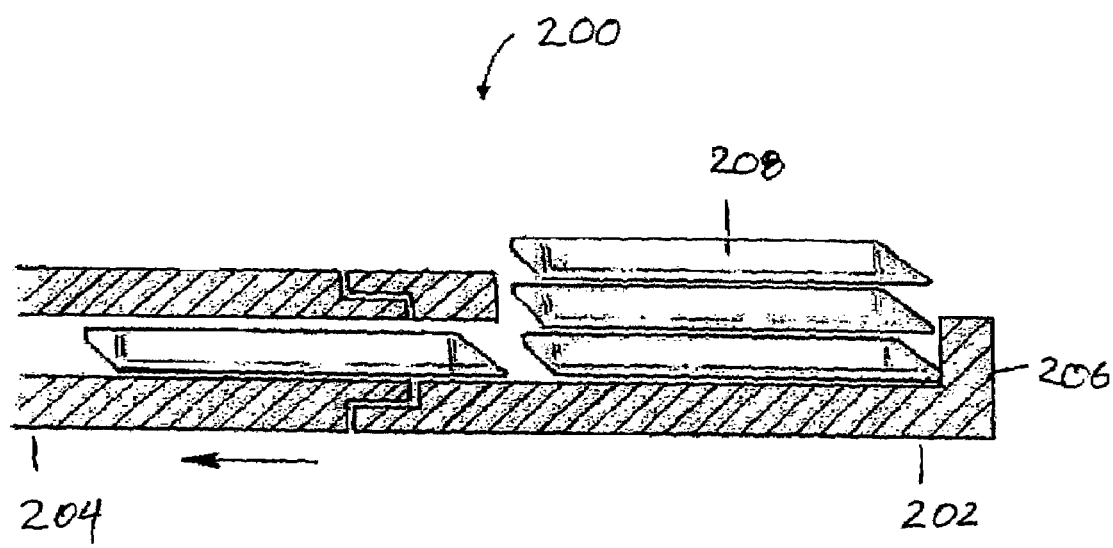
FIG. 20 is a side cross-sectional view of a detachable tip for a wafer inserter according to any of the prior embodiments.

A detachable tip wafer inserter embodiment, as seen in FIG. 20, includes a distal tip 202 of a wafer inserter 200, which can be configured like the wafer inserter of FIG. 3 or FIG. 4, for instance. The distal tip 202 is detachable from the main portion 204 of the inserter. One advantage provided by the detachable tip is that the height of the wafer column is not altered when the wafer inserter is removed. The tip 202 is preferably manufactured of the same material as the wafers. Thus, in a preferred embodiment, if the wafers 208 are manufactured of PMMA, the distal tip 202 of the wafer inserter 200 is manufactured of PMMA. Alternately, the distal tip 202 may be manufactured of an implant grade metal or other medical grade implantable material. The distal tip 202 has a fixed distal shoulder 206 that holds the first wafer in place while the second wafer is inserted under the first. The height of the distal shoulder 206 may provide a stop for one wafer, or it may provide a stop for two or more wafers. The considerations applicable to the height of the distal catch apply to the height of the distal shoulder as well.

Figure 21:
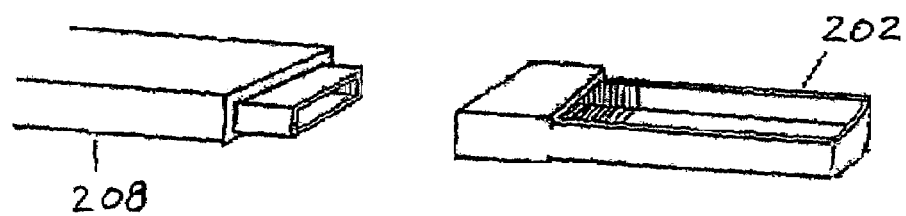
FIG. 21 is a front partial perspective view of the detachable tip depicted in FIG. 20.

The aforementioned '998 Patent discloses a detachable tip embodiment for a wafer insertion apparatus, the description of which is also incorporated herein by reference. In this embodiment, wafers are inserted until the desired height or force is attained, and then, as seen in FIG. 21, the distal tip 202 is then released from the main portion 204 of the wafer inserter and the main portion 204 of the inserter is removed. The distal tip may be press-fit onto the track or may be bonded with an appropriate adhesive. In either case, the interface is designed to support the forces generated while building a wafer column 210, but shear when the extraction plunger is used to remove the wafer inserter. Optionally, the distal tip 202 may be keyed to interlock with the main portion 204 of the wafer inserter. For example, the main portion of the inserter may interlock with the distal tip by spring-loaded hooks that are mechanically compressed when the tip is to be released. Alternately, the hooks may be spring-loaded in the release position and mechanically expanded to engage the distal tip. In another embodiment, the detachable tip may be press-fit onto the wafer inserter or bonded with a weak adhesive. When the wafer inserter is to be removed, a force may be applied using a longer plunger or equivalent mechanism as in the fixed tip wafer inserter to dislodge the removable tip. The track of the wafer inserter may be then removed.

Figure 22:
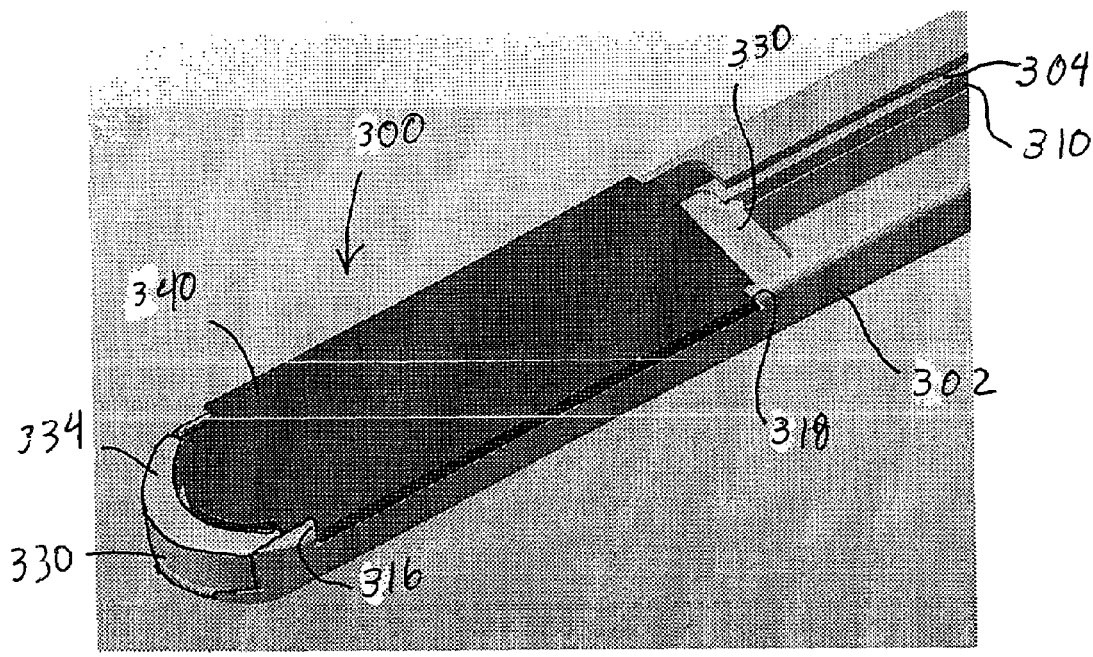
FIG. 22 is a top perspective view of a detachable wafer assembly according to one embodiment of the invention.
Figure 23:
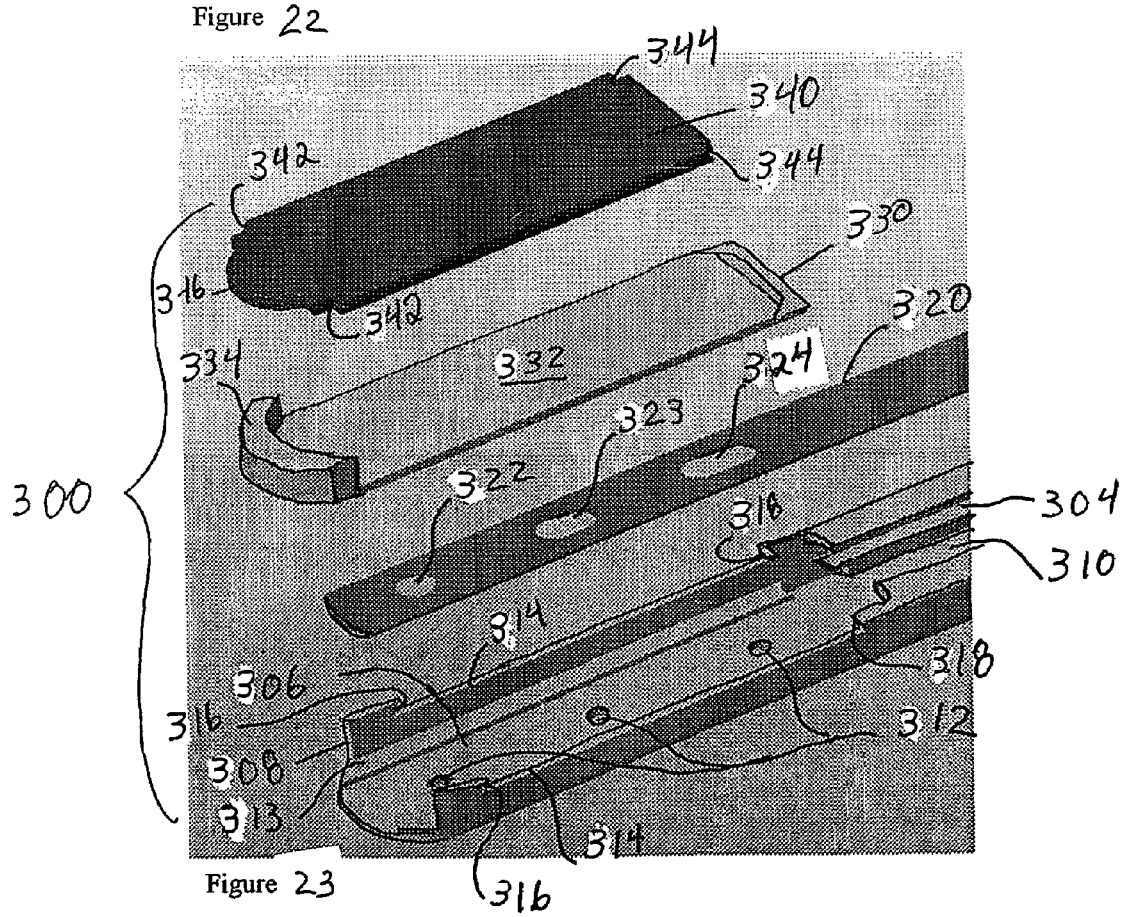
FIG. 23 is a top exploded perspective view of the detachable wafer assembly shown in FIG. 22.
Figure 24:
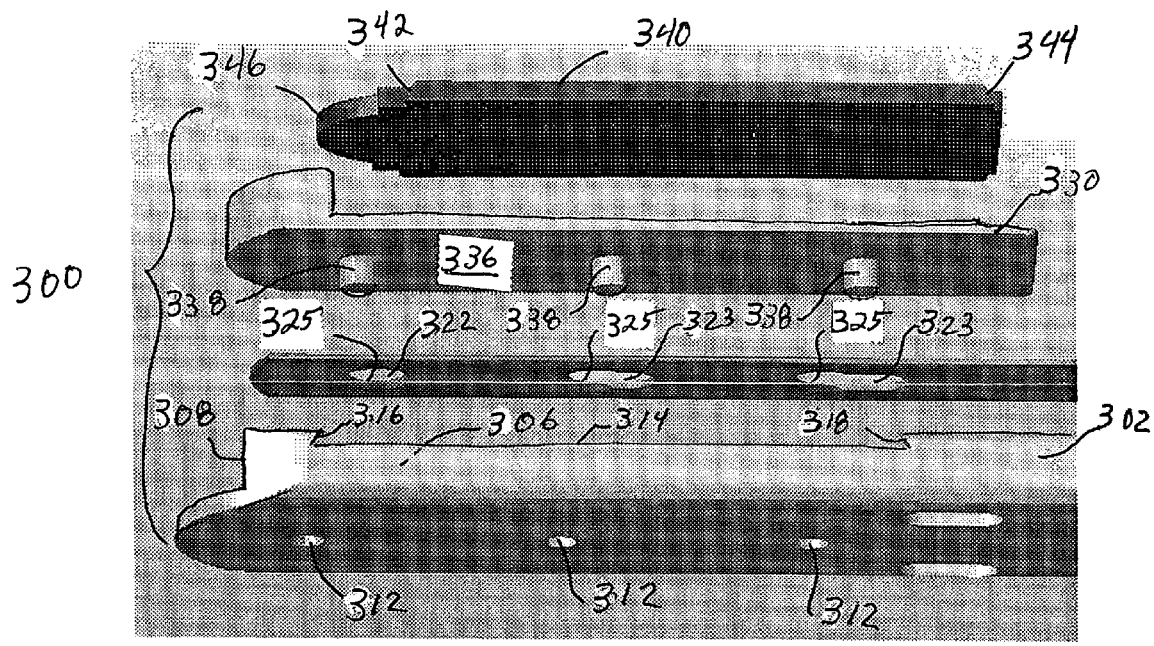
FIG. 24 is a bottom exploded perspective view of the detachable wafer assembly shown in FIG. 22.

An alternative embodiment of a detachable tip wafer insertion apparatus is shown in FIGS. 22–24. The detachable wafer assembly 300 includes a bottom track 302 that can be integrated into the wafer insertion assemblies described above. For instance, the bottom track 120 of the track assembly 33 shown in FIG. 13 can be modified in the form of the bottom track 302 shown in FIGS. 22–24. The bottom track 302 defines a wafer channel 304 along which successive wafers can be advanced, again in the manner disclosed above. The wafer channel extends to an upward facing discharge opening 306 at the distal end of the bottom track. Thus, wafers conveyed along the bottom track are discharged at the opening 306 to form the wafer stack within the body space being distracted. The wafer channel 304 is also open at its end, and specifically at an end opening 308.

The bottom track 302 further defines a cutter channel 310 beneath the wafer channel 304. The cutter channel is configured to slidably receive a slide cutter 320, shown in FIGS. 23–24. The cutter channel extends at least along the length of the bottom track adjacent the distal end thereof and terminates beneath the discharge opening 306 at the end opening 308. At the distal end, and particularly beneath the discharge opening 306, the bottom track 302 defines a base wafer recess 313 that is configured to support the base wafer 330. The base wafer recess 313 is situated at a level above the cutter channel 310 but below the wafer channel 304. Specifically, the depth of the base wafer recess is calibrated so that the top surface 332 of the base wafer 330 resides substantially at the level of the wafer channel 304 so that wafers (such as wafers 208 shown in FIG. 20) conveyed along the channel slide directly on top of the base wafer.

The bottom track also defines top cap slots 314 along the side walls adjacent the discharge opening 306. The forward and rear edges of the slots 314 form chamfered ends 316 and 318, respectively. The slots 314 and ends 316, 318 are configured to support and retain a top cap wafer 340. The top cap wafer includes end chamfers 342, 344 that cooperate or interlock with the corresponding chamfered ends 316, 318 to hold the top cap wafer 340 in position above the discharge opening 306. In addition, the top cap wafer 340 forms an end edge 346 that corresponds to a stop end 334 of the base wafer. Thus, the top cap wafer 340 is held on top of the discharge opening as shown in FIG. 22.

The top cap wafer 340 is configured to release from the top cap slot 314 under pressure from a wafer (such as wafer 208) being advanced along the bottom track 302 underneath the top cap wafer. In other words, as a new wafer moves toward the discharge opening, it moves underneath the top cap wafer 340, dislodging the end chamfers 342, 344 from the chamfered slot ends 316, 318 and moving it upward within the tissue space.

Figure 25:
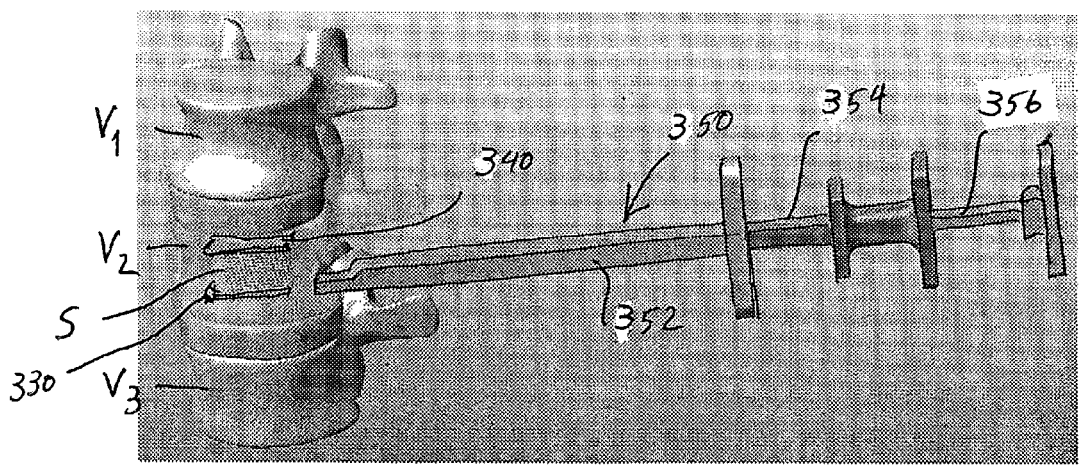
FIG. 25 is a side perspective view of a bone cement delivery system according to a further embodiment of the invention.

In one beneficial feature of the invention, the top cap wafer 340 is larger in dimension and/or area than the wafers conveyed along the apparatus to be added to the wafer stack S (see FIG. 25). Preferably, the top cap wafer has a width or transverse dimension W (FIG. 23) that is at least larger than width of the subsequently inserted wafers. This larger geometry can create a vertical space or gap G (FIG. 26) along the side of the wafer stack that can be subsequently filled with a biologic material, such as bone cement, bone filler, paste, putty or similar material. In addition, the greater area of the top cap wafer 340 can increase the overall load lifting capacity of the stack by engaging a larger area of the tissue surface to be distracted. In a specific embodiment, the top cap wafer 340 can have a width dimension W that is 1–2 mm wider than the intermediate wafers. This greater dimension can also apply to the overall length of the top cap wafer, alone or in conjunction with a greater width.

In a similar fashion, the base wafer 330 is also preferably larger in area than the intermediate wafers of the stack. As shown in FIG. 23, the base wafer defines an upper support surface 332 that is sized to generally approximate the size of an intermediate wafer, such as a wafer 208. The stop end 334 provides an end surface against which successive wafers bear when they are advanced along the bottom track. The stop end 334 can aid in alignment and placement of the wafers as they are added to the stack. Thus, the stop end can help ensure that the wafer stack is uniform and can prevent any wafers from being askew within the stack. The stop end 334 also helps reduce or even eliminate the reaction force from the standard wafer gun insertion or from the lift forces applied by one wafer to a prior wafer.

In one aspect of the invention, a connection mechanism is provided for releasably connecting the base wafer to the track, and more particularly to the channel defined by the track. Referring to FIG. 24, the underside, or bottom surface 336 of the base wafer 330 can be seen. Specifically, the base wafer includes a number of retention bosses 338 projecting from the bottom surface 336. These retention bosses extend first through openings 322, 323, 324 in the slide cutter 320 disposed beneath the base wafer. The bosses are configured to extend into boss receptacles or bores 312 defined in the cutter channel 310 of the bottom track 302. Preferably, the bosses 338 and bores 312 form a press-fit so that the base wafer 330 is held firmly at the discharge end of the bottom track while the intermediate wafers are being inserted into the tissue space. With this embodiment, the connection mechanism includes the bosses and bores.

Figure 28:
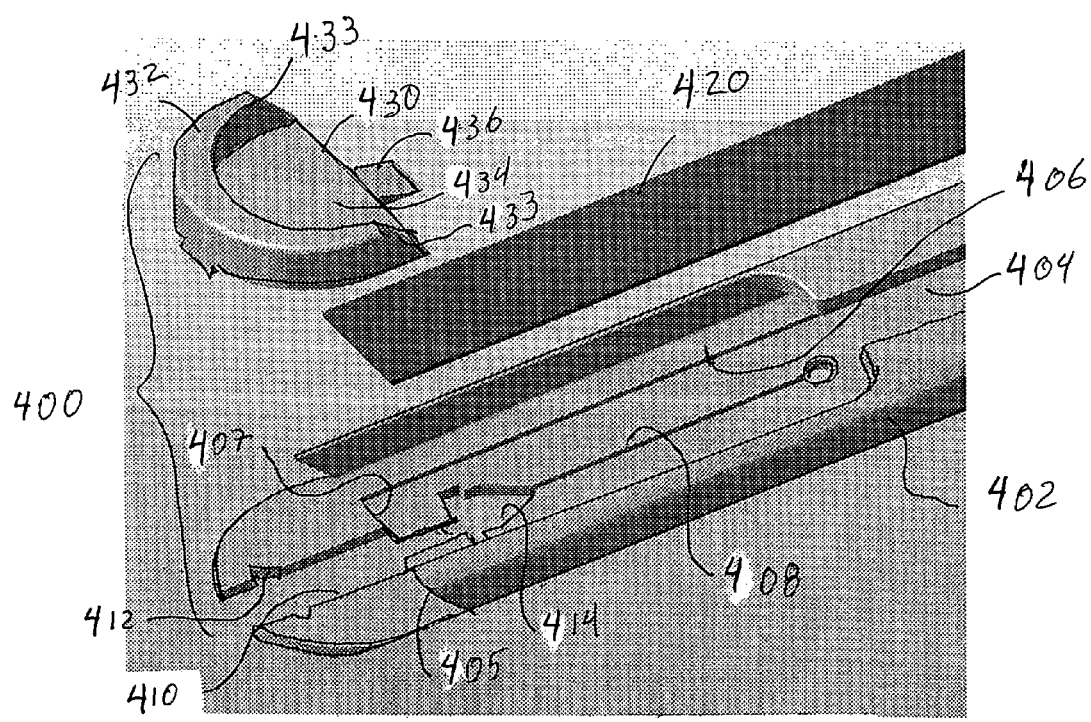
FIG. 28 is a top perspective view of a detachable wafer assembly according to a further embodiment of the invention.

In the illustrated embodiment, the openings 322, 323, 324 are increasingly longer from the distal to the proximal ends of the track 302. This feature facilitates alignment of the openings 322–324 with the bosses 338 and bores 312 when the detachable wafer assembly 300 is constructed. As shown in FIG. 24, the distal ends of the slots 322–324 define cutting edges 325. These cutting edges 325 are configured to sever the bosses 338 from the bottom surface 336 of the base wafer 330. Preferably, the bosses 338 are integral with the remainder of the base wafer, and most preferably formed of the same material. This material is selected so that longitudinal movement of the slide cutter 320 can readily slice through the material of the boss. Thus, once all of the wafers have been installed, the slide cutter 320 can be retracted within the bottom track 302, severing the bosses and freeing the base wafer 330 from the bottom track 302. The bottom track 302 can then be removed, leaving the base wafer behind to anchor the wafer stack, as shown in FIG. 28.

Figure 26:
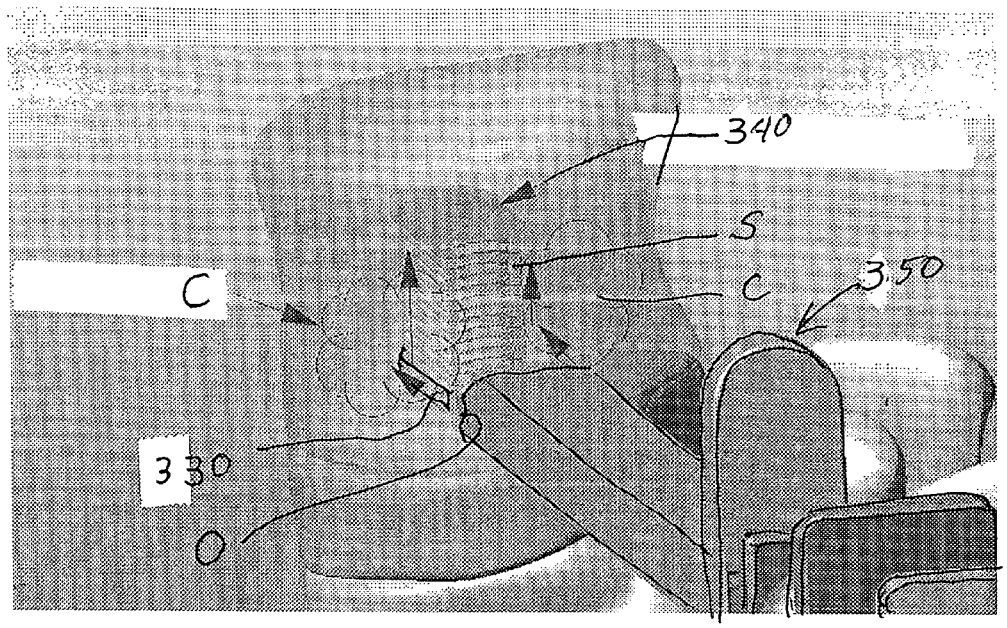
FIG. 26 is an end perspective view of the bone cement delivery system shown in FIG. 25.

As depicted in FIGS. 25–26, a material delivery system 350 can be provided for use once the stack S has been disposed within a tissue space, such as the interior of a vertebral body $V_2$. The system 350 includes a reusable working channel cannula 352 that can extend through an opening O formed in the vertebral wall (which is also the same opening through which the wafers are inserted). A cannulated material delivery port 354 is concentrically disposed within the cannula of the cannula 352 and is preferably pre-filled with the biologic material, such as bone cement C. A plunger 356 is provided to inject the biologic material C into the space surround the wafer stack S.

Figure 27:
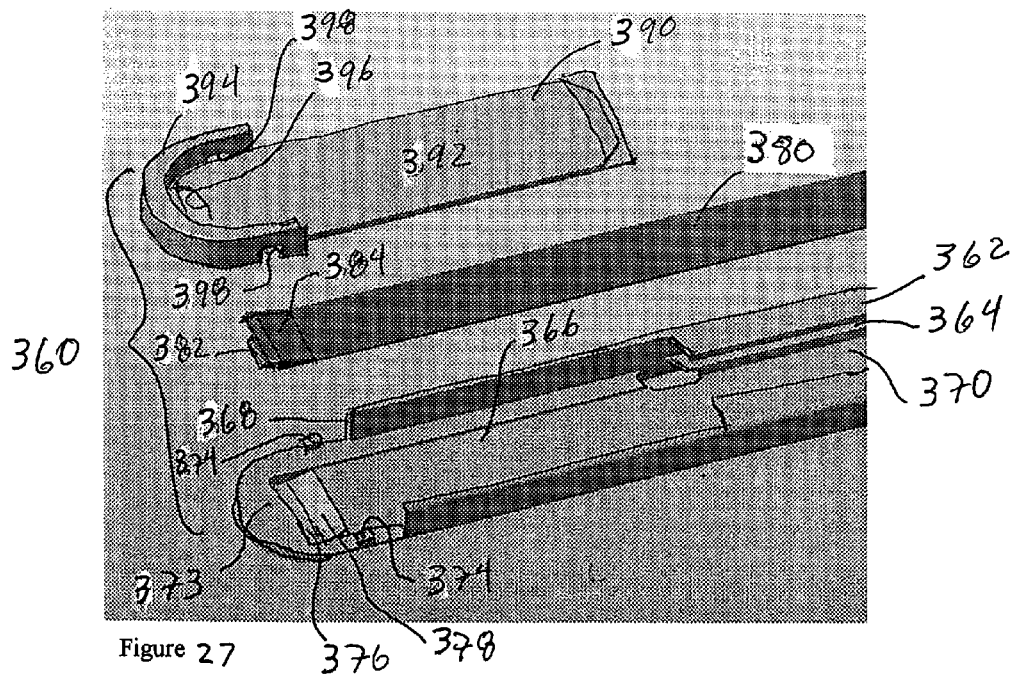
FIG. 27 is a top perspective view of a detachable wafer assembly according to another embodiment of the invention.

A further embodiment of a detachable wafer assembly is shown in FIG. 27. In this embodiment, an assembly 360 includes a bottom track 362 that is similar to the track 302 described above in that it includes a wafer channel 364, a wafer discharge opening 366 and an end opening 368. The bottom track 362 further defines a release plate channel 370 that is substantially contiguous with and beneath the wafer channel 364. The release plate channel 370 terminates in a release ramp 378 and catch slot 376 within the discharge opening 366.

Like the prior bottom track, the bottom track 362 also defines a base wafer recess 373 that supports a base wafer 390. However, unlike the prior embodiment, the base wafer 390 is supported with a portion of the wafer projecting from the end of the bottom track, and specifically from the end opening 368 of the bottom track 362. Like the base wafer in the prior embodiment, the base wafer 390 defines a wafer support surface 392 that supports the successive stack of wafers deployed through the insertion apparatus. The base wafer 390 also includes a stop end 394 that serves the same function as the stop end for the base wafer 330 described above.

The base wafer also defines a retention slot 396 and retention notches 398 at opposite sides of the stop end 394. The retention notches interlock with retention posts 374 projecting upward from the bottom track 362 adjacent the release ramp 378. The retention slot is configured to receive a portion of the distal end of the release plate 380, such as the release ramp 384. The underside of the release plate 380 forms a catch 382 that is configured to reside within the catch slot 376 at the base of the release ramp 378 to hold the release plate 380 in position during wafer insertion.

The base wafer 390 is held to the bottom track by the interaction of the retention slot 396 and retention notches 398 with the corresponding ramp 384 and posts 374. Once all of the wafers have been inserted, the release plate 380 is retracted toward the proximal end of the bottom track 362. As the plate 380 moves back, the catch 382 travels up the release ramp 378, pushing the ramp 384 of the release plate 380 up against the underside of the base wafer 390. This movement dislodges or disassociates the base wafer 390 from the release plate 380 or more specifically releases the notches 398 from the retention posts 374. The bottom track 362 can then be removed without disturbing the base wafer in situ.

Figure 29:
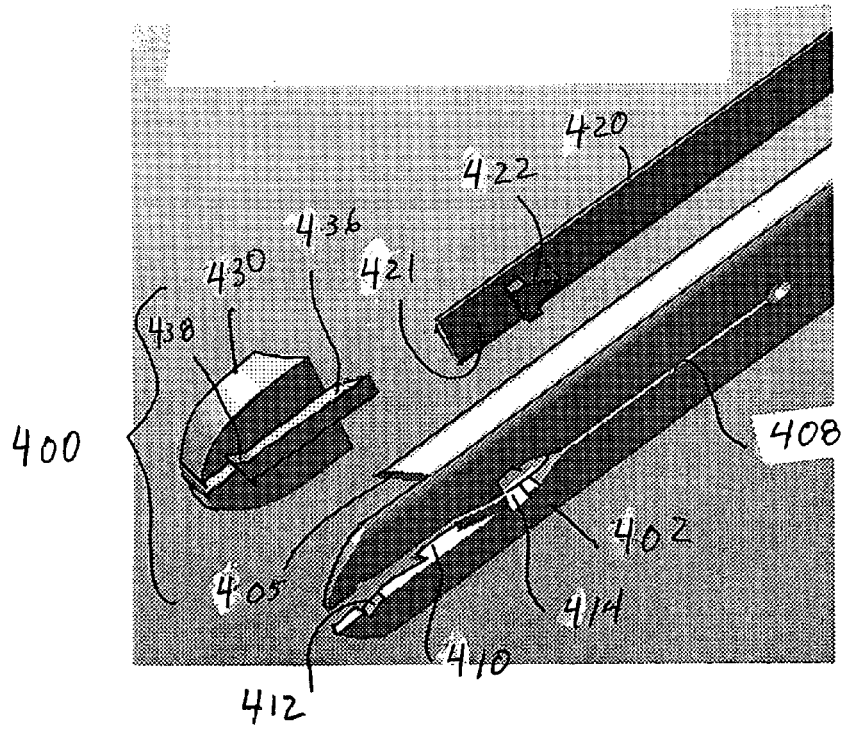
FIG. 29 is a bottom perspective view of the detachable wafer assembly shown in FIG. 28.

In yet another embodiment, a detachable wafer assembly 400 includes a bottom track 402, a release plate 420 and a base wafer 430, as shown in FIGS. 28–29. The bottom track 402 defines a wafer channel 404, terminating in an end opening 405 and a wafer discharge opening 406. The bottom track 402 includes a split line 408 extending longitudinally along the track from the end opening 405. The split line is configured to form a base wafer retention slot 410 and a retention notch 412 at the end opening 405. Upstream of the slot 410 is a release plate retention notch 414.

The features of the split line 408 are configured to interlock with corresponding features on the underside of the release plate 420 and base wafer 430. In particular, the release plate 420 has a bottom surface 421 that includes a release cam 422 projecting therefrom. This release cam 422 is shaped to fit snugly within the notch 414 in the split line 408 when the assembly is initially put together. Similarly, the base wafer 430 includes a linear key 436 and flared key 438 formed on its underside. These keys also fit snugly within the retention slot 410 and notch 412 to hold the base wafer in association with the bottom track 402 during initial assembly. In addition, the bottom track defines angled edges at the end openings 405 that mate with corresponding angled edges 433 of the stop end 432 of the base wafer. The base wafer further forms a wafer support surface 434 that supports at least a portion of subsequent wafers stacked on top of the base wafer.

As with the prior embodiments, the base wafer 430 is initially engaged to the bottom track 402 when the detachable wafer assembly 400 is introduced into the tissue site. As successive wafers are introduced along the wafer channel 404, the stop end 432 of the base wafer helps maintain the alignment of the stack. Once the last wafer has been inserted, the release plate 420 is withdrawn toward the proximal end of the bottom track. As the release plate 420 moves, the release cam 422 is dislodged from the retention notch 414 and moves upstream along the split line 408. This movement causes the bottom track to split apart along the split line 408, thereby widening the retention slot 410 and retention notch 412. As the slot and notch widen, the keys 436 and 438 are freed from the split line so that the base wafer can be disassociated or dislodged from the bottom track. The bottom track can then be withdrawn, leaving the base wafer and the rest of the wafer stack within the distraction site.

Figure 7:
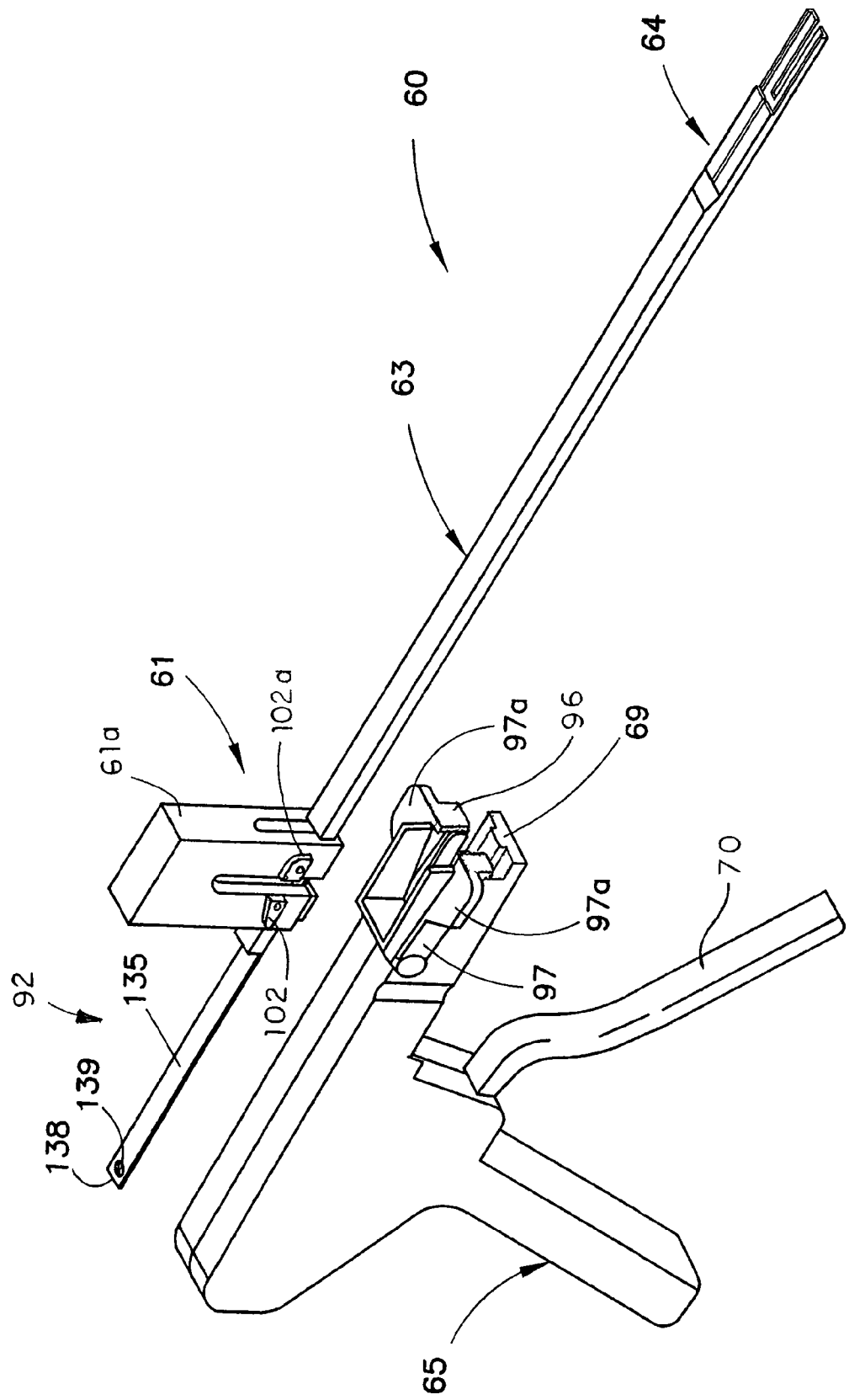
FIG. 7 is a perspective, partially exploded view of a wafer insertion apparatus in accordance with a further embodiment of the invention.

As explained above, the detachable wafer assemblies 300 and 400 can be used with a wafer insertion apparatus, such as the apparatus 35 of FIG. 6 or the apparatus 60 of FIG. 7. The bottom tracks 302 and 402 of the respective assemblies can be integrated with the discharge end, such as discharge opening 122 at the distal discharge end 64 of the apparatus 60. Likewise, the track 63 of the wafer insertion apparatus 60 would be modified to receive the slide cutter 320, the release plate 380 or the release plate 420 and keep it clear beneath the wafer advancement components (such as the components depicted in FIG. 13). A separate triggering mechanism is preferably provided to actuate the cutter or release plates to allow dislodgement of the detachable elements of the wafer assembly.

Figure 30:
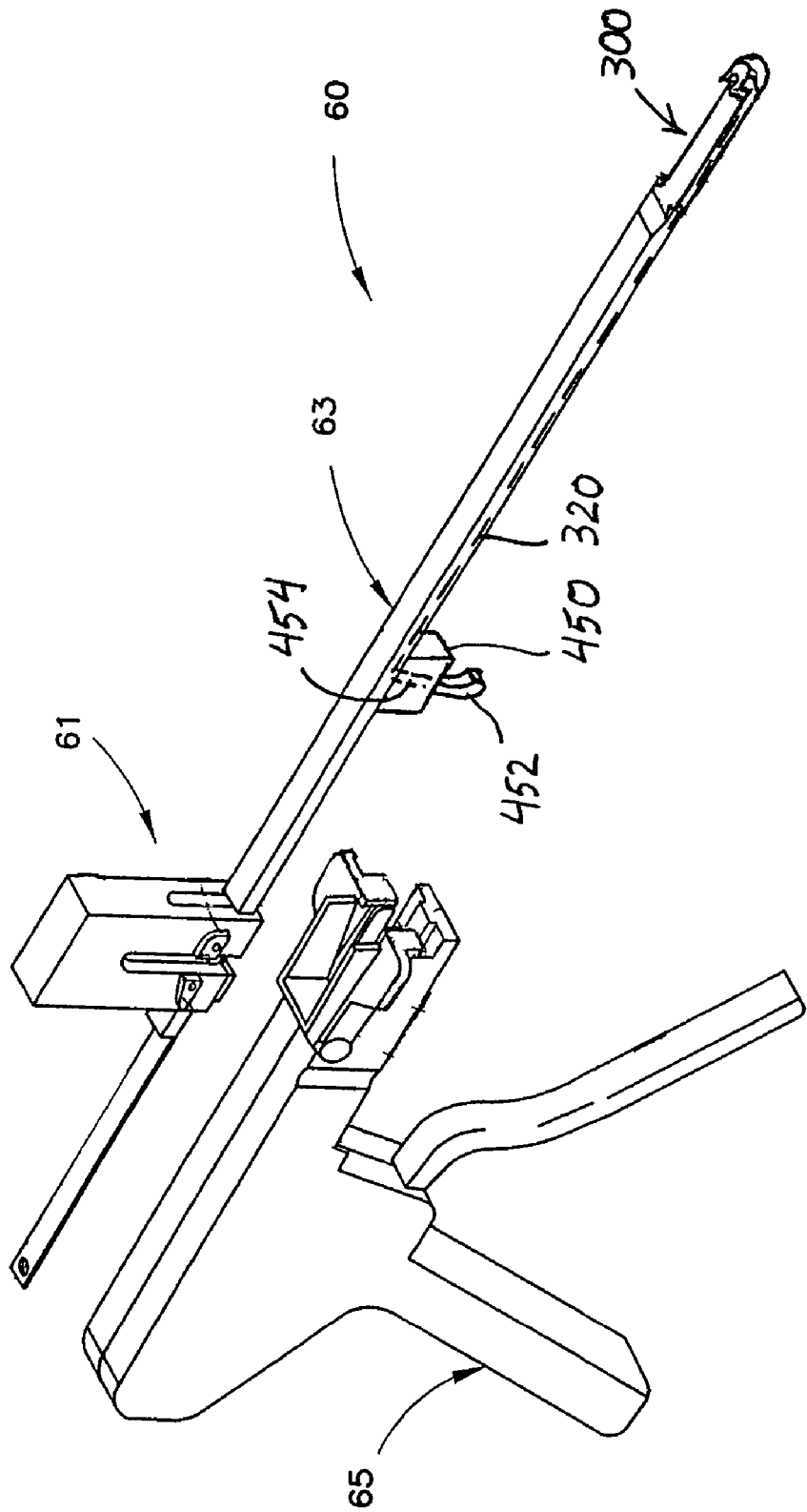
FIG. 30 is a perspective, partially exploded view of a wafer insertion apparatus with a detachable wafer component in accordance with a further embodiment of the invention.

In one example, a detachable wafer assembly 300 is integrated with the track assembly 63 of the insertion apparatus 60, as illustrated in FIG. 30. The detachable wafer assembly includes a slide cutter 320 that extends from the assembly 300 into the bottom track of the track assembly 63, as depicted in dashed lines. A trigger assembly 450 can be mounted to the underside of the track assembly, adjacent the connection between the track assembly and the gun 65. A manual trigger or lever 452 is engaged by a linkage 454 to the proximal end of the slide cutter. Depressing the trigger 452 propels the slide cutter to sever the retention bosses 338, as described above. It is understood that other actuation mechanisms are contemplated to operate the slide cutter or the release plates of the other embodiments.

One advantage of the detachable wafer assemblies of the present FIGS. 22–30 is that the base wafer 334, 390 and 430 provide a positive stop for intermediate wafers being advanced toward the distal end of the assembly. This positive stop ensures that the wafers are stacked in substantial vertical alignment within the body cavity, even if the wafer inserter exerts an excessive axial insertion force on a newly introduced wafer to the stack. A further advantage is that the detachable base wafer ensures that the stack height is not altered when the wafer insertion process is completed.

Providing a top cap wafer, such as wafer 340 and a base wafer 330 with a larger area or width than the intermediate wafers provides additional space immediately surrounding the wafer stack for the introduction of bio-compatible materials. In particular, the larger dimension of the cap wafer helps "clear out" cancellous bone within the body cavity as the cap wafer is pushed upward by subsequently introduced intermediate wafers. Impregnating the stack with a bone cement, for instance, can strengthen the stack and maintain the distraction and support capabilities of the stack.

Preferably, the detachable components of the inventive system are formed of a material similar to the material of the intermediate wafers. These detachable components, such as the base wafer and the top cap wafer, are thus preferably formed of a PMMA, for instance. The base wafer and top cap wafer can be formed with bone ingrowth channels or interstices. Alternatively, one or both of the top cap wafer and base wafer can be formed of an implant grade metal, such as stainless steel or titanium.

While the invention has been illustrated and described in detail in the drawings and foregoing description, the same should be considered as illustrative and not restrictive in character. It is understood that only the preferred embodiments have been presented and that all changes, modifications and further applications that come within the spirit of the invention are desired to be protected.

What is claimed is:

1. An apparatus for sequentially inserting wafers, stackable consecutively one upon another to form a stack extending in a given direction into a body tissue space to be distracted, the apparatus comprising:
   a source of wafers;
   a track assembly connected to said source of wafers and configured to sequentially advance wafers from the source of wafers into the space to be distracted, said track assembly having a distal end and defining a channel at said distal end;
   a base wafer supported within said channel of said track assembly, said base wafer defining a support surface for supporting subsequent wafers advanced thereon by said track assembly; and
   a connection mechanism between said channel and said base wafer configured to releasably connect said base wafer to said channel.

2. The apparatus of claim 1, wherein said connection mechanism includes:
   at least one bore defined in said channel; and
   a corresponding boss projecting from said base wafer and sized for engagement within said bore.

3. The apparatus of claim 2, further comprising a slide cutter slidably disposed within said channel, said slide cutter defining at least one opening therethrough corresponding to said at least one bore and configured to receive said corresponding boss therethrough when said boss is engaged within said bore, said at least one opening configured to sever said boss from said base wafer when said cutter is translated within said channel.

4. The apparatus of claim 3, wherein:
   said channel defines a wafer channel sized for passage of said wafers therethrough;
   said track assembly is configured to support said base wafer beneath said wafer channel; and
   said channel further defines a cutter channel beneath said base wafer when said base wafer is supported on said channel for slidably receiving said slide cutter therein.

5. The apparatus of claim 1, wherein said connection mechanism includes:
   at least one retention post projecting from said channel; and
   a corresponding retention notch defined in said base wafer to engage said retention post when said base wafer is within said channel.

6. The apparatus of claim 5, further comprising a release plate slidably disposed within said channel, said release plate having a surface configured to contact said base wafer and dislodge said corresponding retention notch from said at least one retention post when said release plate is translated within said channel.

7. The apparatus of claim 1, wherein said connection mechanism includes:
   a retention slot defined in said channel; and
   a key projecting from said base wafer and configured to be received within said retention slot when said base wafer is disposed within said channel.

8. The apparatus of claim 7, further comprising:
   a spilt line defined in said channel and intersecting said retention slot; and
   a release plate slidably disposed within said channel and having an element extending through said spilt line and configured to separate said channel along said split line as said release plate is translated within said channel, whereby said retention slot expands as said channel is separated to release said key from said retention slot.

9. The apparatus of claim 1, wherein said base wafer and said wafers from said source of wafers are formed of the same material.

10. The apparatus of claim 9, wherein said material is a biologic material.

11. The apparatus of claim 10, wherein said material is PMMA.

12. The apparatus of claim 1, wherein:
   said channel defines a wafer channel sized for passage of said wafers therethrough; and
   said track assembly is configured to support said base wafer beneath said wafer channel.

13. The apparatus of claim 1, wherein said base wafer defines a stop at an end of said base wafer and arranged to stop advancement of said wafers across said support surface.

14. The apparatus of claim 1, wherein said channel has an open end at said distal end.

15. The apparatus of claim 14, wherein said base wafer defines a stop at an end of said base wafer, said base wafer supported on said channel with said stop at said open end.

16. The apparatus of claim 1, wherein said connection mechanism includes an element movably disposed within said track assembly and operable to separate said base wafer from said channel.

17. The apparatus of claim 16, wherein:
said connection mechanism includes at least one bore and a corresponding boss, configured to be received within said at least one bore, defined between said base wafer and said channel; and
said element is a plate disposed between said base wafer and said channel and defining at least one opening therethrough sized to receive said corresponding boss therethrough when said corresponding boss is engaged within said at least one bore, said plate movable within said channel to sever said boss.

18. The apparatus of claim 17, wherein said at least one bore is defined in said channel and said corresponding boss projects from said base wafer.

19. The apparatus of claim 17, wherein said at least one opening and said corresponding boss define a press-fit engagement.

20. An apparatus for sequentially inserting wafers, stackable consecutively one upon another to form a stack extending in a given direction into a body tissue space to be distracted, the apparatus comprising:
a base wafer defining a support surface for supporting subsequent sequentially inserted wafers thereon;
a track assembly configured to receive sequentially advanced wafers from a source of wafers into the space to be distracted, said track assembly having a distal end and defining a channel at said distal end, said channel having a portion supporting said base wafer within said channel and a wafer channel sized for passage of the sequentially inserted wafers to a position directly above said base wafer in the given and direction; and
a connection mechanism between said channel and said base wafer configured to releasably connect said base wafer to said channel during sequential insertion of the stackable wafers, said connection mechanism including;
a male-female connection defined between said base wafer and said channel; and
a release plate slidably disposed within said track assembly and configured to break said male-female connection.

21. The apparatus of claim 20, wherein:
said channel has an open end at said distal end; and
said base wafer includes a stop at an end thereof that is positioned at said open end when said base wafer is supported on said portion of said channel to prevent passage of sequentially inserted wafers beyond said distal end.

22. The apparatus of claim 20, wherein:
said male-female connection includes at least one boss and a corresponding bore for receiving said boss, defined between said base wafer and said channel; and
said release plate includes a slide cutter defining at least one opening to receive said at least one boss therethrough and configured to sever said boss when said slide cutter is retracted into said track assembly.

23. The apparatus of claim 20, wherein:
said male-female connection includes at least one retention post and a corresponding retention notch configured to receive said notch defined between said base wafer and said channel; and
said release plate is disposed between said base wafer and said channel and defines opposing surfaces configured to separate said base wafer from said channel to thereby dislodge said at least one retention post from said corresponding retention notch.

24. The apparatus of claim 20, wherein:
said male-female connection includes a retention slot and a key configured to project into said retention slot, defined between said base wafer and said channel; and
said release plate includes a distal end configured to separate said slot to permit removal of said key therefrom.

25. An apparatus for sequentially inserting wafers, stackable consecutively one upon another to form a stack extending in a given direction into a body tissue space to be distracted, the apparatus comprising:
a track assembly configured to sequentially advance wafers from a source of wafers into the space to be distracted, said track assembly having a distal end and defining a channel opening at said distal end;
a base wafer supported on said track assembly at said distal end, said base wafer defining a support surface for supporting subsequent wafers received from said channel; and
a connection mechanism releasably connecting said base wafer to said track assembly, said connection mechanism having a first configuration holding said base wafer as subsequent wafers are inserted thereon through said channel and movable to a different second configuration operable to separate said base wafer from said track assembly.

26. The apparatus of claim 25, wherein said connection mechanism includes:
at least one boss projecting from said base wafer; and
a plate movably disposed within said track assembly, said plate defining at least one opening corresponding to said at least one boss and configured to sever said boss when said plate is moved within said track assembly.

27. The apparatus of claim 26, wherein said connection further includes at least one bore defined in said track assembly configured and arranged to receive a corresponding one of said at least one boss therein.

28. The apparatus of claim 27, wherein said plate is disposed between said base wafer and said track assembly.

29. The apparatus of claim 25, wherein said connection mechanism includes:
at least one retention post and a corresponding retention notch, configured to engage said at least one retention post, defined between said base wafer and said track assembly; and
a release plate disposed between said base wafer and said track assembly and movable to disengage said corresponding retention notch from said at least one retention post.

* * * * *

UNITED STATES PATENT AND TRADEMARK OFFICE
CERTIFICATE OF CORRECTION

PATENT NO. : 6,997,929 B2
APPLICATION NO. : 10/846235
DATED : February 14, 2006
INVENTOR(S) : Manzi et al.

It is certified that error appears in the above-identified patent and that said Letters Patent is hereby corrected as shown below:

In the Claims:

Claim 8, line 2 (Column 22, line 41): replace "spilt" with --split--

Claim 8, line 5 (Column 22, line 44): replace "spilt" with --split--

Signed and Sealed this

Twentieth Day of May, 2008

JON W. DUDAS
*Director of the United States Patent and Trademark Office*